United States Patent
Belgorod

(10) Patent No.: US 10,195,224 B2
(45) Date of Patent: *Feb. 5, 2019

(54) THERAPEUTIC COMPOSITIONS AND METHODS OF TREATMENT WITH CAPSIANOSIDE-TYPE COMPOUNDS

(71) Applicant: BMB Patent Holding Corporation, New York, NY (US)

(72) Inventor: Barry Miles Belgorod, New York, NY (US)

(73) Assignee: BMB Patent Holding Corporation, New York, NY (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/934,888

(22) Filed: Nov. 6, 2015

(65) Prior Publication Data

US 2016/0129029 A1 May 12, 2016

Related U.S. Application Data

(62) Division of application No. 11/925,604, filed on Oct. 26, 2007, now abandoned.

(60) Provisional application No. 60/863,302, filed on Oct. 27, 2006.

(51) Int. Cl.
| | |
|---|---|
| C07H 3/04 | (2006.01) |
| C07H 15/10 | (2006.01) |
| A61K 31/7016 | (2006.01) |
| A61K 31/7028 | (2006.01) |
| A61K 36/81 | (2006.01) |
| A61K 31/70 | (2006.01) |
| A61K 45/06 | (2006.01) |

(52) U.S. Cl.
CPC .......... *A61K 31/7016* (2013.01); *A61K 31/70* (2013.01); *A61K 31/7028* (2013.01); *A61K 36/81* (2013.01); *A61K 45/06* (2013.01); *C07H 3/04* (2013.01); *C07H 15/10* (2013.01)

(58) Field of Classification Search
None
See application file for complete search history.

(56) References Cited

U.S. PATENT DOCUMENTS

| | | |
|---|---|---|
| 4,313,958 A | 2/1982 | LaHann |
| 4,400,398 A | 8/1983 | Coenen et al. |
| 4,564,633 A | 1/1986 | LaHann et al. |
| 4,592,912 A | 6/1986 | Nickolaus |
| 4,702,916 A | 10/1987 | Geria |
| 5,021,450 A | 6/1991 | Blumberg |
| 5,166,373 A | 11/1992 | Takayanagi et al. |
| 5,660,830 A | 8/1997 | Anderson |
| 5,665,360 A | 9/1997 | Mann |
| 5,741,510 A | 4/1998 | Rolf et al. |
| 5,762,963 A | 6/1998 | Byas-Smith |
| 5,788,982 A | 8/1998 | Nadoolman et al. |
| 5,827,886 A | 10/1998 | Hersh |
| 5,854,291 A | 12/1998 | Laughlin et al. |
| 5,856,361 A | 1/1999 | Holt et al. |
| 5,869,533 A | 2/1999 | Holt |
| 5,885,597 A | 3/1999 | Botknecht et al. |
| 5,910,512 A | 6/1999 | Conant |
| 5,958,418 A | 9/1999 | Johnson Prillerman |
| 6,060,060 A | 5/2000 | Belgorod |
| 6,071,507 A | 6/2000 | Zuluaga et al. |
| 6,086,888 A | 7/2000 | Belgorod |
| 6,159,473 A | 12/2000 | Watkins et al. |
| 6,197,823 B1 | 3/2001 | Barr et al. |
| 6,201,014 B1 | 3/2001 | Gardiner |
| 6,277,398 B1 | 8/2001 | Caruso |
| 6,284,797 B1 | 9/2001 | Rhodes |
| 6,333,421 B1 | 12/2001 | Yazawa et al. |
| 6,348,501 B1 | 2/2002 | Holt et al. |
| 6,465,022 B1 | 10/2002 | Torres |
| 6,534,086 B1 | 3/2003 | Krumhar |

(Continued)

FOREIGN PATENT DOCUMENTS

| | | |
|---|---|---|
| EP | 2096927 A2 | 9/2009 |
| JP | 02138289 | 5/1990 |

(Continued)

OTHER PUBLICATIONS

Ettmayer, P. et al., Journal of Medicinal Chemistry, "Lessons Learned from Marketed and Investigational Prodrugs", 2004, vol. 47, No. 10, 2393-2404.*
Stella, V.J., Expert Opin. Ther. Patents, "Prodrugs as therapeutics", 2004, vol. 14, No. 3, pp. 277-280.*
Testa, B., Biochemical Pharmacology, "Prodrug research: futile or fertile?", 2004, vol. 68, pp. 2097-2106.*
Wolff, M. E., Burger's Medicinal Chemistry and Drug Discovery, Fifth Edition, vol. I: Principles and Practice, pp. 975-977.*
Hashimoto et al., "Effect of capsianoside, a diterpene glycoside, on tight-junctional permeability," Biochimica et Biophysica Acta (1997) 281-290, 1323(2).

(Continued)

*Primary Examiner* — Shaojia A Jiang
*Assistant Examiner* — Bahar Craigo
(74) *Attorney, Agent, or Firm* — Carter, DeLuca, Farrell & Schmidt, LLP

(57) ABSTRACT

The present invention discloses the use of certain compounds as therapeutic agents, and in particular as analgesics and anti-inflammatory agents. Such compounds include, for example, certain diterpene monoglycosides and diterpene diglycosides. The compounds of the present invention may be synthesized or isolated from the fruit of the genus *Capsicum*, and in particular may be isolated from sweet bell peppers (*C. annuum*). Pharmaceutically-acceptable salts, enantiomers, diasteriomers, racemic mixtures, enantomerically-enriched mixtures, solvates, and prodrug s of such compounds are also disclosed. Pharmaceutical compositions and methods of using such compounds, including pharmaceutical compositions and methods of using such compounds in combination with one or more active ingredients, are also disclosed.

5 Claims, 11 Drawing Sheets

(56) References Cited

U.S. PATENT DOCUMENTS

| | | | |
|---|---|---|---|
| 6,552,024 | B1 | 4/2003 | Chen et al. |
| 6,573,302 | B1 | 6/2003 | Holt et al. |
| 6,579,543 | B1 | 6/2003 | McClung |
| 6,586,018 | B1 | 7/2003 | Fasano |
| 6,589,513 | B2 | 7/2003 | Lesky et al. |
| 6,593,370 | B2 | 7/2003 | Tamura et al. |
| 6,653,352 | B2 | 11/2003 | Barr et al. |
| 6,689,399 | B1 | 2/2004 | Dickson |
| 6,812,254 | B1 | 11/2004 | Barr et al. |
| 6,919,095 | B2 | 7/2005 | Torres |
| 6,949,260 | B2 | 9/2005 | Krumhar |
| 9,090,645 | B2 | 7/2015 | Belgorod |
| 2001/0011083 | A1 | 8/2001 | Barr et al. |
| 2004/0185126 | A1 | 9/2004 | Mayeux |
| 2005/0026847 | A1 | 2/2005 | Jacobs et al. |
| 2008/0103102 | A1 | 5/2008 | Belgorod |

FOREIGN PATENT DOCUMENTS

| | | |
|---|---|---|
| JP | 4-198135 | 7/1992 |
| JP | 2006212007 A | 8/2006 |
| WO | 2008052183 A2 | 5/2008 |

OTHER PUBLICATIONS

Iorizzi et al., Proceedings of the Phytochemical Society of Europe (2000), 46 (Flavour and Fragrance Chemistry), 77-85, Coden: APPEDR; ISSN:0309-9393.

Iorizzi et al., "New Glycosides from *Capsicum annuum*L. Var. *acumination*. Isolation, Structure Determination, and Biological Activity" Journal of Agricultural and Food Chemistry (2001) 2022-2029, 49(4).

Iorizzi et al., "Antimicrobial furostanol saponins from the seeds of *Capsicum annuum* L var. *acuminatum*." Journal of Agricultural and Food Chemistry (2002) 4310-4316, 50(15).

Izumitani, "Novel Acyclic Diterpene Glycosides, Capsianosides A-F and I-VI from Capsicum Plants (Solanaceous Studies. XVI)" Chem. Pharm. Bull. (1990) 1299-1307, 28(5).

Shimizu et al., ACS Symposium Series (998), 708 (Functional properties of Proteins and Lips), 265-278, CODEN: ACSMC8; ISSN: 0097-6156.

Song et al., "Enhanced infection of an X4 strain of HIV-1 due to capping and colocalization of CD4 and CXCR4 induced by capsianoside G, a diterpene glysoside." Biochem. Biophys. Res. Commun. (2001) 423-429, 283(2).

Yahara et al., "New Acyclic Diterpene Glycosides, capsianosides VI, G and H from the Leaves and Stems of *Capsicum annuum* L." Chem. Pharm. Bull. (1991) 3258-3260, 39(12).

Yahara et al., "New acyclic diterpene glycosides from Capsicum plants", Tennen Yuki Kagobutsu Toronkai Koen Yoshishu (1988), 30, 173-9, CODEN: TYKYDS.

Yahara, "A Novel Acyclic Diterpene Glycoside, Capsianside A, From*Capsicum annum* Var. *fasciculatum*" Tetrahedron Letters (1988) 1943-1946, 29(16).

Fuller, "The human pharmacology of capsaicin." Archives Internationales de Pharmacodynamie et de Therapie (1990) 147-156, 303.

Dworkin et al., "Advances in neuropathic pain: diagnosis, mechanisms, and treatment recommendations." Archives of Neurology (2003) 1524-1534, 60(11).

Lee et al., "Acyclic diterpene glycosides, capsianosides VIII, IX, X, XIII, XV and XVI from the fruits of Paprika *Capsicum annuum* L. var. *grossum* Bailey and Jalapeno *Capsicum annuum* L. var. *annuum*." Chem. Pharm. Bull. (2006) 1365-1369, 54(10).

Govindarajan, "Capsicum production, technology, chemistry, and quality. Part 1: History, botany, cultivation, and primary processing." Critical Reviews in Food Science and Nutrition (1985) 109-176, 22(2).

De Marino et al., "New constituents of sweet *Capsicum annuum* L. fruits and evaluation of their biological activity." Journal of Agricultural and Food Chemistry (2006) 7508-7516, 54(20).

Bucar et al., "Flavonoids from Phlomis Nissolii" Phytochemistry (1998) 573-575, 48(3).

Cordell et al., "Capsaicin: identification, nomenclature, and pharmacotherapy." The Annals of Pharmacotherapy (1993) 330-336, 27(3).

European Patent Appl. No. 07854460.8 Search Report (dated Nov. 13, 2009).

European Patent Appl. No. 07854460.8 Search Opinion (dated Nov. 25, 2009).

European Patent Appl. No. 07854460.8 Third Party Observations (Jun. 29, 2010).

International Appl. No. PCT/US07/82717 International Search Report (dated Feb. 15, 2008).

International Appl. No. PCT/US07/82717 Written Opinion (dated Feb. 15, 2008).

International Appl. No. PCT/US07/82717 International Preliminary Report on Patentability (dated Apr. 28, 2009).

Derwent English abstract translation of JP4-198135 (1992). Retrieved May 1, 2015.

Remington: The Science and Practice of Pharmacy, 19th Edition, editor Alfonso R. Gennaro, published by Mack Publishing Company (1995) p. 82, 1615 and 1648.

Definition of "moiety" from the Merriam Webster Online Dictionary [online], [Retrieved on Jan. 6, 2010]. Retrieved from the internet <http://www.merriam-webster.com/dictionary/moiety>.

Vippagunta, S.R., Brittain, H.G., Grant, D.J.W. (2001) Crystalline solids. Advanced Drug Delivery Reviews, vol. 48, pp. 3-26.

Wolff et al. Burger's Medicinal Chemistry and Drug Discovery (1994) Wiley-Interscience, Fifth Edition, vol. 1: Principles and Practice, pp. 975-977.

\* cited by examiner

Formula IV

Chemical Formula: $C_{32}H_{52}O_{14}$
Molecular Weight: 660.75

Formula II

Chemical Formula: $C_{26}H_{42}O_9$
Molecular Weight: 498.61

THERAPEUTIC COMPOSITIONS AND METHODS OF TREATMENT WITH CAPSIANOSIDE-TYPE COMPOUNDS

RELATED APPLICATION DATA

This application is a divisional of U.S. patent application Ser. No. 11/925,604, filed Oct. 26, 2007, which claims priority to U.S. Provisional Patent Application No. 60/863,302, filed on Oct. 27, 2006, the entirety of each of which is hereby incorporated by reference.

FIELD OF THE INVENTION

The present invention relates to analgesic compositions and methods with compounds known as capsianosides and related compounds. The compounds may be synthesized or they may be isolated from the fruit of the genus *Capsicum*, in particular *Capsicum annuum*. This invention further relates to the therapeutic uses of such compounds as analgesics and as anti-inflammatory agents.

BACKGROUND OF RELATED TECHNOLOGY

A primary focus of drug research is the development of analgesics for pain management. Analgesics render sensory pathways insensible or less sensible to pain, whereas anesthetics act on all sensory pathways rendering them insensible to pain, temperature, touch, proprioception and skeletal muscle tone. As such, although anesthetics can be used for pain management, their utility is limited by their inhibition of these other sensory pathways. For example, it may be desired to control a patient's pain associated with an oral mucosal lesion without interfering with senses of touch, proprioception (to avoid biting of the tongue) or taste (so as not to interfere with appetite), which is not generally possible with topical anesthetics (for example, Benzocaine) which are not able to selectively inhibit pain. The use of analgesics to control pain in such circumstances is therefore desirable.

Analgesics are generally classified as either narcotic (opioids) or non-narcotic. Narcotic analgesics primarily act on the central nervous system and carry potentially life-threatening side-effects such as addiction, impaired higher cortical function and depressed respiration. As a result, their use is regulated and they may only be prescribed by licensed practitioners. Non-narcotic analgesics include salicylates, such as aspirin; acetaminophen; and non-steroidal anti-inflammatory drugs ("NSAIDS"), such as cyclooxygenase-2 ("Cox-2") inhibitors. Such non-narcotic analgesics can be limited in their ability to control pain and may have the side effects of chemical irritation, anticoagulation, myocardial infarction and stroke. Accordingly, there is a continuing need for the discovery and development of new analgesics, and in particular non-narcotic analgesics, that are useful for the localized management of pain without an undesirable side effects profile.

In this regard, various plant-derived compounds have been investigated for their analgesic properties. For example, capsaicin, a vanillyl alkaloid that is the source of pungency in hot peppers, has been used to treat the pain of arthritis, osteoarthritis, and various peripheral neuropathies. See, for example, Cordell and Araujo, *The Annals of Pharmacotherapy*, (1993) 27:330; Levinson, (January/February 1995) *The Sciences*, pp. 13-15. However, the therapeutic usefulness of capsaicin is limited due to an adverse side effects profile that includes burning sensations and erythema, and such side effects may persist over time. By way of further example, extracts of sweet bell peppers (*Capsicum annuum*) have been shown to exhibit analgesic properties (see, for example, U.S. Pat. Nos. 6,060,060 and 6,086,888), but the specific compounds responsible for such analgesic effects have not been identified. Furthermore, as such extracts must be derived from naturally-occurring fruit, their production and practical use is limited.

Moreover, certain capsianosides (diterpene glycosides) that occur naturally in sweet bell peppers have been identified, for example capsianosides A-F and I-V reported both by Izumitani et al. ("Novel Acyclic Diterpene Glycosides, Capsianosides A-F and I-V from *Capsicum* Plants" (Solanaceous Studies, XVI) *Chem. Pharm. Bull.* (1990), 38(5): 1299-1307) and by Iorizzi et al. ("New Glycosides from *Capsicum annuum* L. Var. *acuminatum*. Isolation, Structure Determination, and Biological Activity" *J. Agric. Food Chem.* (2001), 49:2022-2029), some of which have been shown to inhibit the activity of angiotensin-converting enzyme in vitro, and therefore may be useful as anti-hypertensive agents (see, for example, published Japanese Patent Application No. 02-138289 (1990)). However, no experimental or clinical data is known to have been reported that establishes the therapeutic utility of such compounds.

SUMMARY OF THE INVENTION

The present invention is directed to certain compounds and their use as therapeutic agents, and in particular as analgesics and anti-inflammatory agents. Such compounds include, for example, various diterpene monoglycosides and diterpene diglycosides which may be synthetically or semi-synthetically produced, or which may be isolated from the fruit of the genus *Capsicum*, and in particular may be isolated from sweet bell peppers (*C. annuum*). Pharmaceutically-acceptable salts, enantiomers, diastereomers, racemic mixtures, enantomerically-enriched mixtures, solvates, and prodrugs of such compounds are also included in the present invention. Pharmaceutical compositions, combinations of compounds of the present invention and other therapeutic ingredients, such as analgesics and anti-inflammatory agents, are also provided by the present invention, as are methods of using such pharmaceutical compositions, compounds and combinations. Objects of the present invention include providing pharmaceutical compositions, compounds, and combinations for the treatment of pain, discomfort and inflammation, in a safe and effective manner.

In one aspect, the present invention is directed to pharmaceutical compositions that includes a therapeutically effective amount of a compound according to Formula I:

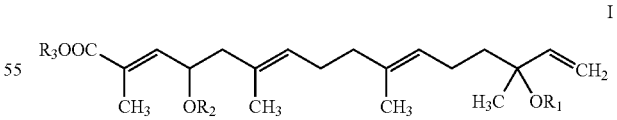

I or a pharmaceutically-acceptable salt, enantiomer, diasteriomer, racemic mixture, enantomerically-enriched mixture, solvate, or prodrug of Formula I, in a pharmaceutically effective carrier, wherein $R_1$ is a carbohydrate moiety; $R_2$ is H or $C(O)R_4$; $R_3$ is H, a carbohydrate moiety, or a substituted or unsubstituted $C_1$-$C_{20}$ group; and $R_4$ is a substituted or unsubstituted $C_1$-$C_{20}$ group. In certain embodiments, $R_1$ and $R_3$ are independently selected from the group consisting of glucose, galactose, rhamnose, xylose, and arabinose; $R_1$ is glucose, $R_2$ and $R_3$ are each H; and each of $R_2$, $R_3$, and $R_4$ independently comprises one or more aromatic rings. The compound may be present in an amount that is therapeutically effective to treat analgesia or reduce inflammation in a mammal.

In certain embodiments, the compound according to Formula I is a compound of Formula II:

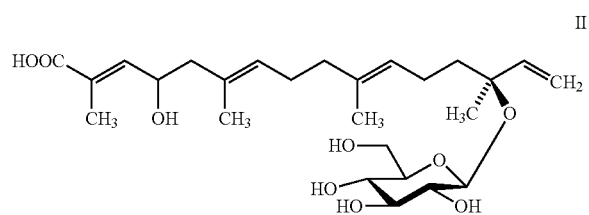

II

In certain embodiments, a prodrug of a compound according to Formula I is a compound according to Formula III:

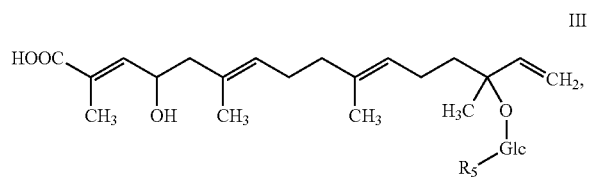

III wherein $R_5$ is a hydrolyzable sugar, such as glucose.

In certain embodiments, a prodrug of a compound according to Formula I is a compound of Formula IV:

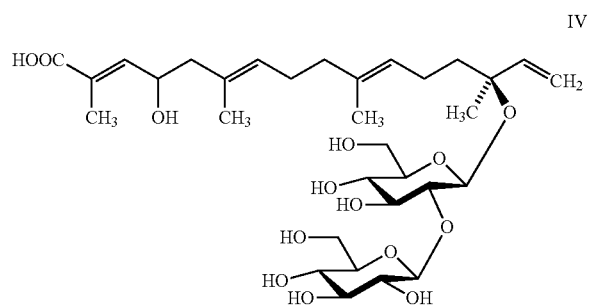

IV

Further, pharmaceutical compositions of the present invention may be in the form of an immediate-release, controlled-release, or sustained-release orally-administrable composition, such as a pill, tablet, capsule, gelcap, lozenge, throat spray, solution, emulsion, cream, paste, gel, cough drop, dissolvable strip, lollipop, or gum; in the form of a topically-administrable composition, such as a liquid solution, liquid spray, emulsion, cream, paste, gel, lotion, foam, or impregnated dressing; in the form of an occularly-administrable composition, such as eye-drops; and may be administered to the sinuses, throat, or lungs, for example in the form of inhalable particles, an inhalable solution, droplets, or an aerosol.

Compounds of the of the present invention may be produced synthetically or semi-synthetically; or may be isolated and purified from a naturally occurring organism, such as from a fruit of the genus *Capsicum*, such as *C. annuum*, in which case they may be isolated and purified away from the cellular debris of the naturally occurring organism.

In certain embodiments, the present invention is directed to pharmaceutical compositions including one or more therapeutic agents in combination with a compound of the present invention, such as an analgesics and/or anti-inflammatory agents, for example an NSAID selected from the group consisting of salicylates, acetaminophen, ibuprofen and COX-2 inhibitors.

In another aspect, the present invention is directed to pharmaceutical compositions including a therapeutically effective amount of a compound according to Formula II in a pharmaceutically effective carrier. The compound of Formula II may be provided in an analgesically-effective amount, and may be provided in combination with one or more therapeutic agents, such as those discussed above.

In another aspect, the present invention is directed to pharmaceutical compositions including a therapeutically effective amount of a compound according to Formula I, as defined above, or a pharmaceutically-acceptable salt, enantiomer, diasteriomer, racemic mixture, enantomerically-enriched mixture, solvate, or prodrug of Formula I, in a pharmaceutically effective carrier, and which is present in an analgesically-effective amount. The substituents and compounds of Formula I may be those noted above. Such compounds may be present in an analgesically-effective amount of between about 0.01 mg to about 500 mg per unit dose, and between about 1 mg to about 100 mg per unit dose. Such pharmaceutical compositions may be administered as noted above.

In another aspect, the present invention is directed to a method for effecting analgesia or reducing inflammation in a mammal, comprising administering to a patient in need thereof a pharmaceutical composition comprising a therapeutically effective amount, which may be an analgesically-effective amount, of a compound according to Formula I, defined above, or a pharmaceutically-acceptable salt, enantiomer, diasteriomer, solvate, or prodrug of Formula I, in a pharmaceutically effective carrier. The substituents and compounds of Formula I may be those noted above. Such methods may include administering compounds of the present invention in the manners noted above alone or in combination with other noted therapeutic agents, and in a therapeutically effective amount of between about 0.01 mg to about 500 mg per unit dose, and between about 1 mg to about 100 mg per unit dose.

DETAILED DESCRIPTION OF THE INVENTION

Figure 1:
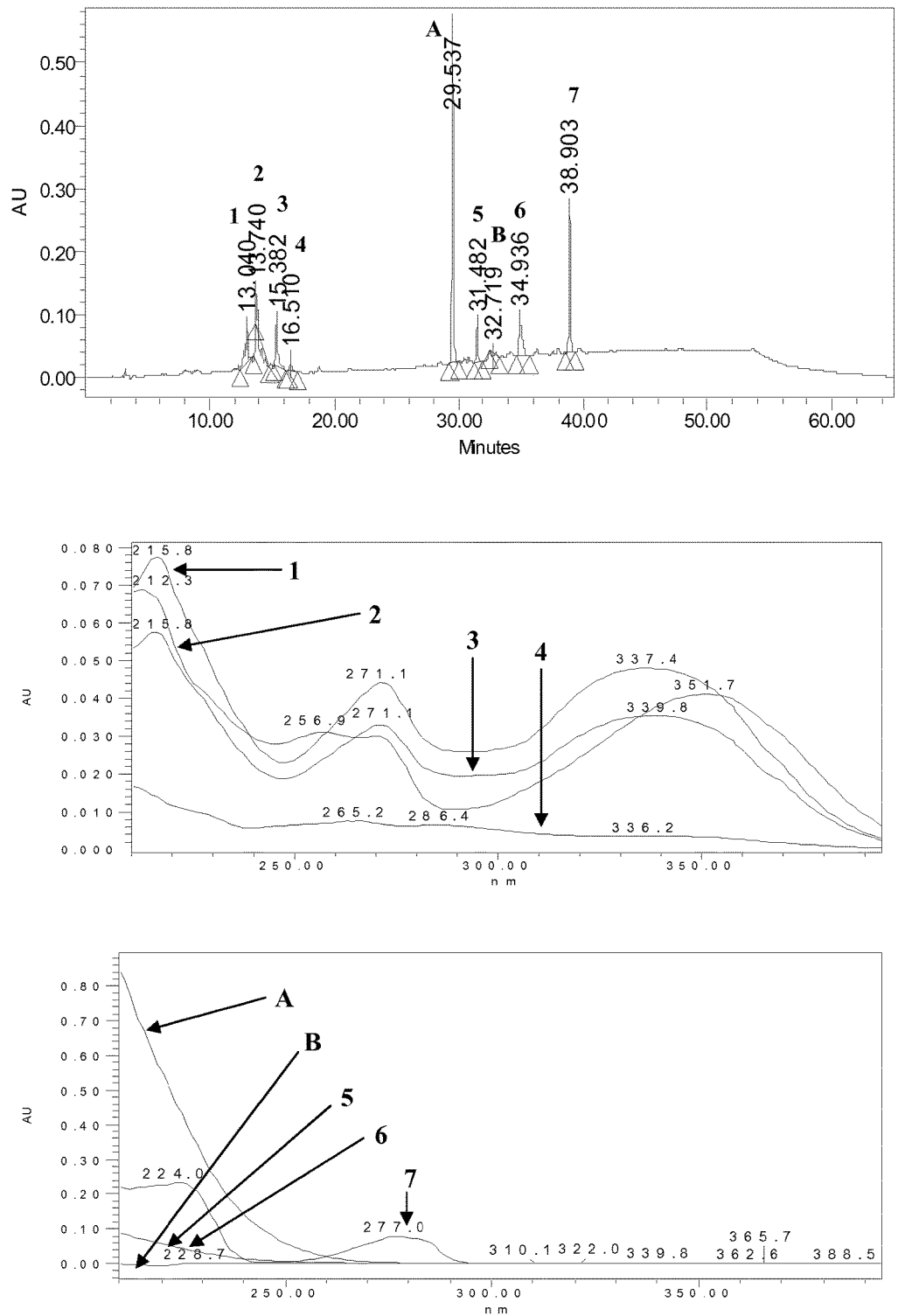
FIG. 1 shows HPLC chromatograms and UV spectra of fraction BMBW-M40i.

The present invention is directed to the discovery of certain compounds, including certain diterpene monoglycosides and diterpene diglycosides, as therapeutic agents, and in particular as analgesics for the prevention, treatment and management of pain, and as anti-inflammatory agents.

As described herein, such compounds have been isolated, identified, and shown to have therapeutic utility. The identification and characterization of these compounds, pharmaceutical compositions including such compounds, and methods of making and using such compounds and pharmaceutical compositions of the present invention, are the result of research efforts described herein that stem from the unexpected discovery that the puree or juice of sweet peppers exhibits an analgesic effect on inflamed pharyngeal mucosa, without the burning sensation or pungency that accompanies the use of capsaicin or the purees or juices of peppers exhibiting pungency.

In this regard, the present invention is directed in certain embodiments to pharmaceutical compositions including a therapeutically effective amount of a compound according to Formula I:

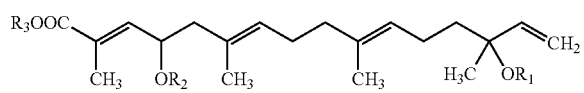

I or a pharmaceutically-acceptable salt, enantiomer, diasteriomer, solvate, or prodrug of Formula I, in a pharmaceutically effective carrier, wherein $R_1$ is a carbohydrate moiety; $R_2$ is H or $C(O)R_4$; $R_3$ is H, a carbohydrate moiety, or a substituted or unsubstituted $C_1$-$C_{20}$ group; and $R_4$ is a substituted or unsubstituted $C_1$-$C_{20}$ group. The carbohydrate moiety of $R_1$ may be, for example and without limitation, glucose, galactose, rhamnose, xylose, or arabinose. In certain embodiments, $R_2$, $R_3$, or $R_4$ may each independently include one or more aromatic rings.

In certain embodiments, the present invention is directed to pharmaceutical compositions including a therapeutically effective amount of a compound of Formula II:

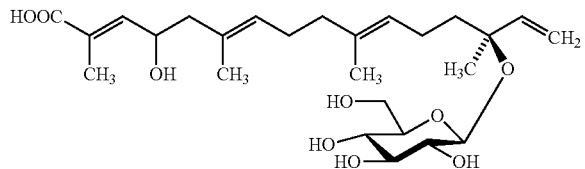

II

In certain embodiments, the present invention is directed to pharmaceutical compositions including a prodrug of a compound according to Formula I, such as a compound according to Formula III:

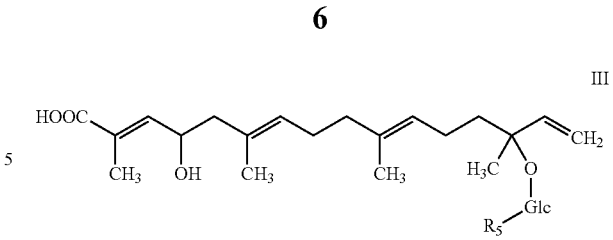

III wherein $R_5$ is a hydrolyzable sugar, such as Glc. Upon hydrolysis by enzymes such as pancreatic or salivary disaccharidases, or by conditions in the stomach or other locations in vivo, a compound according to Formula III may yield a compound with a single Glc unit, such as a compound of Formula II.

In certain embodiments, such a prodrug is a compound of Formula IV:

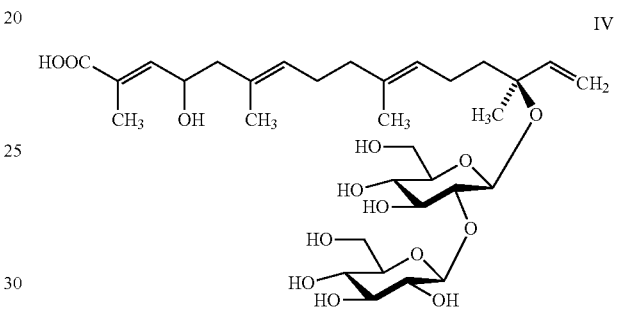

IV

As used in the present invention without limitation, the term "prodrug" is given its conventional and generally art-recognized definition as a compound that is provided to a patient in a generally inactive form (or in a form with substantially reduced activity), and which is converted into an active, or more active, drug in vivo, such as through enzymatic cleavage. The resulting active drug is generally referred to as a "metabolite" of the prodrug. Without being bound to any particular theory, it is believed that in the present invention certain compounds according to Formula III are prodrugs of certain compounds according to Formula I, such that when a compound according to Formula III is introduced into or on a human, it will react under normal metabolic conditions to yield a compound according to Formula I. For example, it is believed that a compound of Formula IV is a prodrug of a compound of Formula II. Moreover, additional prodrugs that are within the scope of the present invention include, without limitation, compounds with hydrolyzable groups on the free hydroxyl group or ester groups at the carboxylic acid. Certain prodrugs may, for example, independently meet the limitations of Formula I, while other prodrugs meet the limitations of Formula I only after conversion into their active form.

As used in the present invention, to state that a composition "includes a compound according to (or of) a particular Formula, or a pharmaceutically-acceptable salt, enantiomer, diasteriomer, racemic mixture, enantomerically-enriched mixture, solvate, or prodrug of such Formula", specifically means that such composition may include either a single compound falling within such definition, or may include more than one compound falling within such definition. For example, a pharmaceutical composition of the present invention that includes a "therapeutically effective amount of a compound according to Formula I, or a pharmaceutically-acceptable salt, enantiomer, diasteriomer, racemic mixture, enantomerically-enriched mixture, solvate, or prodrug of Formula I" may include a single compound according to Formula I (such as a compound of Formula II), or may, for example, include a compound of Formula II in combination with another compound that meets the above definition, for example a compound of Formula IV. Likewise, pharmaceutical compositions of the present invention may further include other compounds, for example they may include a compound of Formulas II and a compound of Formula IV in combination with a salt according to Formula I, etc. As will be appreciated by one of skill in the art, pharmaceutical compositions of the present invention may include any number of compounds in combination that fall within the provided definitions, so long as they are therapeutically or otherwise useful as intended.

As used in the present invention, to state that a compound is present in a "therapeutically effective amount" refers to an amount that is sufficient to effect a desired physiological change in a mammal, as that term is conventionally used and will be recognized by one of skill in the art. For example, to state that a compound is present "in an amount that is therapeutically effective to effect analgesia", means, without limitation, that the compound is present in an amount that results in the alleviation or elimination of pain and/or discomfort in a mammal and/or inflammation, as determined qualitatively or quantitatively. Likewise, to state that a compound is present "in an amount that is therapeutically effective to reduce inflammation" means, without limitation, that the compound is present in an amount that results in the alleviation or elimination of inflammation in a mammal suffering from an inflammatory condition, as determined qualitatively or quantitatively. Such conditions which may be alleviated or eliminated by compounds and compositions of the present invention may be acute or chronic.

Pharmaceutical compositions of the present invention generally include a therapeutically effective amount of a compound according to Formula I, or a pharmaceutically-acceptable salt, enantiomer, diasteriomer, solvate, or prodrug of Formula I, in a pharmaceutically effective carrier. As used in the present invention, the term "pharmaceutically acceptable salts" refers to salts prepared, for example and without limitation, from pharmaceutically acceptable non-toxic bases including inorganic bases and organic bases. Salts derived from inorganic bases include, for example, aluminum, ammonium, calcium, copper, ferric, ferrous, lithium, magnesium, manganic salts, manganous, potassium, sodium, zinc, and the like. Salts derived from pharmaceutically acceptable organic non-toxic bases include, for example, salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Pharmaceutical compositions including a compound according to Formula I, or a pharmaceutically-acceptable salt, enantiomer, diasteriomer, solvate, or prodrug of Formula I, in a pharmaceutically effective carrier, are useful, for example, for the relief of pain, fever and inflammation of a variety of conditions, including rheumatic fever, symptoms associated with influenza or other viral infections; common cold; low back and neck pain; dysmenorrhea; headache; toothache; sprains and strains; myositis; neuralgia; synovitis; arthritis, including rheumatoid arthritis and degenerative joint diseases (e.g., osteoarthritis); gout and ankylosing spondylitis; bursitis; burns; injuries; and pain and inflammation following surgical and dental procedures, as illustrated and suggested by the present Examples. In addition, compositions and compounds of the present invention may inhibit cellular neoplastic transformations and metastic tumor growth, and hence may be useful in the treatment of cancer.

Moreover, pharmaceutical compositions including a compound according to Formula I, or a pharmaceutically-acceptable salt, enantiomer, diasteriomer, solvate, or prodrug of Formula I, are expected to be useful in therapeutic combinations with known therapeutic compounds, for example analgesics and anti-inflammatory agents. For example, analgesics expected to have therapeutic utility in combination with compounds of the present invention include, but are not limited to, NSAIDS such as the salicylates; acetaminophen; ibuprophen; and COX-2 inhibitors.

Pharmaceutical compositions including compounds according to Formula I, or pharmaceutically-acceptable salts, enantiomers, diasteriomers, solvates, or prodrugs of Formula I, may be administered to a patient in need thereof in any acceptable form in dosage unit formulations that employ conventional non-toxic pharmaceutically acceptable carriers, adjuvants and vehicles that permit such compositions of the present invention to have their desired therapeutic effect. For example, such compositions may be in an orally-administrable form; a topical form; may be administered to the sinuses, throat, lungs, eyes, ears, vagina and/or rectum; or may be administered parenterally.

Pharmaceutical compositions of the present invention that are intended for oral and/or topical use may be in the form of a pill, tablet, gelcap, or hard or soft capsule (each of which may be in an immediate, sustained or time-release formulation); lozenge; throat spray; solution; emulsion; cream; ointment; impregnated dressing; foam; paste; gel; cough drop; dissolvable strip; jelly; mouthwash; gargle; lollipop; gum; aqueous or oily suspension, dispersible powder/granules; syrup; and/or elixir, and may be prepared according to any method known in the art for the manufacture of pharmaceutical compositions. Such compositions may further contain one or more agents selected from the group consisting of sweetening agents, flavoring agents, coloring agents and preserving agents in order to provide pharmaceutically elegant and palatable preparations. By dissolvable strip is meant a sheet of material that can be placed in the mouth to dissolve and release the active ingredient. Such dissolvable strips are also known as flavor strips or oral care strips. Dissolvable strips are often carbohydrate-based. Tablets typically contain the active ingredient in admixture with non-toxic pharmaceutically acceptable excipients which are suitable for the manufacture of such tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example, magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

With respect to capsules, in hard gelatin capsule formulations the active ingredient(s) may be mixed with an inert solid diluent, for example, calcium carbonate, calcium phosphate or kaolin; and in soft gelatin capsule formulations the active ingredient(s) may be mixed with water or an oil medium, for example peanut oil, liquid paraffin, or olive oil.

Aqueous suspensions typically contain the active material in admixture with excipients suitable for the manufacture of such aqueous suspensions. Such excipients may be suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents, such as a naturally-occurring phosphatide (e.g., lecithin), condensation products of an alkylene oxide with fatty acids (e.g., polyoxyethylene stearate), condensation products of ethylene oxide with long chain aliphatic alcohols (e.g., heptadecaethylene-oxycetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives, for example ethyl, n-propyl, or p-hydroxybenzoate; one or more coloring agents; one or more flavoring agents; and/or one or more sweetening agents, such as sucrose, saccharin or aspartame.

Oily suspensions may be formulated by suspending the active ingredient in a vegetable oil, such as arachis oil, olive oil, sesame oil or coconut oil; or in mineral oil, such as liquid paraffin. Such oily suspensions may also contain a thickening agent, such as beeswax, hard paraffin or cetyl alcohol. Sweetening agents, such as those set forth above, and flavoring agents, may also be added to provide a palatable oral preparation. Such compositions may be preserved by the addition of an anti-oxidant, such as ascorbic acid.

Dispersible powders and granules suitable for preparation of an aqueous suspension by the addition of water typically provide the active ingredient in admixture with a dispersing or wetting agent, a suspending agent and one or more preservatives. Suitable dispersing or wetting agents and suspending agents are exemplified by those aforementioned. Additional excipients, for example sweetening, flavoring and coloring agents, may also be present.

Pharmaceutical compositions of the present invention may also be in the form of oil-in-water emulsions. In such preparations, the oily phase may be a vegetable oil (e.g., olive oil or arachis oil), a mineral oil (e.g., liquid paraffin), or mixtures of such vegetable and mineral oils. Suitable emulsifying agents may be naturally-occurring phosphatides, such as soy bean, lecithin, esters or partial esters derived from fatty acids and hexitol anhydrides (e.g., sorbitan monooleate), and condensation products of such partial esters with ethylene oxide (e.g., polyoxyethylene sorbitan monooleate). Such emulsions may also contain sweetening and flavoring agents.

Syrups and elixirs may be formulated with sweetening agents, such as glycerol, propylene glycol, sorbitol or sucrose. Such formulations may also contain a demulcent, a preservative, and flavoring and/or coloring agents. Pharmaceutical compositions of the present invention may also be in the form of a sterile injectable aqueous or oleagenous suspension, which may be formulated according to methods known in the art using, for example, suitable aforementioned dispersing or wetting agents, and suspending agents. Such a sterile injectable preparation may also be a sterile injectable solution or suspension in a non-toxic parenterally-acceptable diluent or solvent, such as a solution in 1,3-butane diol. Acceptable vehicles and solvents that may be employed include, for example, water, Ringer's solution and isotonic sodium chloride solution. Additionally, sterile, fixed oils may be employed as a solvent or suspending medium, such as a bland fixed oil, including synthetic mono- or diglycerides. Fatty acids such as oleic acid, may also be used in the preparation of injectables.

As aforementioned, the inventive compounds and pharmaceutical compositions may be administered in a controlled or sustained release system. Such systems include, for example, the use of a pump (see, for example, Langer and Sefton, (1987) CRC *Crit. Ref. Biomed.* 14:201; Buchwald et al. (1980), *Surgery* 88:507; Saudek et al. (1989), *N. Engl. J. Med.* 321:574), and more typically (with respect to oral formulations such as pills, tablets, etc.), the use of polymeric materials (see, for example, *Medical Applications of Controlled Release*, Langer and Wise (eds.) (1974), CRC Pres., Boca Raton, Fla.; *Controlled Drug bioavailability, Drug Product Design and Performance*, Smolen and Ball (eds.) (1984), Wiley, New York; Ranger and Peppas, J. (1983), *Macromol. Sci. Rev. Macromol. Chem.* 23:61; Levy et al. (1985), *Science* 228:190; During et al. (1989). *Ann. Neurol.* 25:351; Howard et al. (1989), *J. Neurosurg.* 71:105). Other means of effecting controlled release involve, for example, placing the therapeutic composition in proximity of the therapeutic target, thus requiring only a fraction of the systemic dose (see, for example, Goodson, *Medical Applications of Controlled Release*, (1984) vol. 2, pp. 115-138). Other controlled release systems which may be employed include those reviewed by Langer (*Science* (1990) 249: 1527-1533).

Pharmaceutical compositions including compounds of Formula I, or pharmaceutically-acceptable salts, enantiomers, diasteriomers, racemic mixtures, enantomerically-enriched mixtures, solvates, or prodrugs of Formula I, may also be administered in the form of rectal suppositories. Such compositions may be prepared by mixing the active compound with a suitable non-irritating excipient which is solid at ordinary temperatures but liquid at rectal temperature, and will therefore melt in the rectum to release the active compound. Suitable rectal suppository materials include cocoa butter and polyethylene glycols.

For topical administration of the inventive compositions and compounds, a lozenge; throat spray; solution; emulsion; cream; ointment; impregnated dressing; foam; paste; gel; cough drop; dissolvable strip; jelly; mouthwash; gargle; lollipop; gum; aqueous or oily suspension, dispersible powder/granules; syrup; and/or elixir may be employed.

Pharmaceutical compositions and compounds of the present invention may also be administered occularly, such as in the form of eye-drops, ointments, sprays or conjunctival timed-release inserts. Administration of the inventive pharmaceutical compositions to the sinuses, throat, or lungs may be in the form of inhalable particles, inhalable solution, droplets, inhalation sprays, or aerosol. Further, such compositions may be administered parenterally, such as by subcutaneous injection, intravenously, intramuscularly, intrasternally, or by various infusion techniques.

Pharmaceutical compositions of the present invention include, for example, analgesically-effective amounts and/or amounts effective to reduce inflammation, of compounds according to Formula I, or pharmaceutically-acceptable salts, enantiomers, diasteriomers, racemic mixtures, enantomerically-enriched mixtures, solvates, or prodrugs of Formula I, and may contain between about 0.01 mg to about 500 mg per unit dose of such compounds. In one embodiment, the amount is between about 1 mg to about 100 mg per unit dose.

The dosage regimen for pharmaceutical compositions of the present invention will, of course, vary depending upon known factors, such as the pharmacodynamic characteristics of the particular agent and its mode and route of administration; the species, age, sex, general health, medical condition, diet, and body weight of the recipient; the nature and extent of the symptoms; the kind of concurrent treatment; the frequency of treatment; the time of administration; route of administration, the renal and hepatic function of the patient, and the effect desired. A physician (or veterinarian in such case as the inventive compositions are use in the treatment of non-human animals) can determine and prescribe the effective amount of the drug required to prevent, counter, or arrest the progress of the disease state.

Moreover, the amount of active ingredient that may be combined with carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

Once formulated, pharmaceutical compositions of the present invention may be used without limitation for various therapeutic uses, including analgesia and reducing inflammation. For examples, such compositions may be used to treat pain and/or discomfort by administration to an individual experiencing pain or discomfort, and may be used to treat inflammatory conditions by administration to an individual exhibiting an inflammatory condition. In one embodiment, compositions according to the present invention are administered to treat one or more symptoms of a cold or flu. Such symptoms include sore throat, eyes, ears, or sinuses. Alternatively, such compositions may be used to treat pain due to abrasions, rash, or minor cuts or burns. For example, in one embodiment, compositions of the present invention are impregnated in adhesive bandages to provide relief from the discomfort of sores or blisters. In another embodiment, compositions of the present invention are applied topically or intramuscularly to provide relief from muscular or joint pain, or relief from neuropathy. Administration routes also include time-released formulations to provide extended or long-range treatment.

Moreover, compounds according to Formula I, or pharmaceutically-acceptable salts, enantiomers, diasteriomers, racemic mixtures, enantomerically-enriched mixtures, solvates, or prodrugs of Formula I, may be entirely natural in origin, or entirely synthetic, or a modified form of a naturally-occurring compound (i.e. semi-synthetic).

Where a compound of Formula I, or a pharmaceutically-acceptable salt, enantiomer, diasteriomer, racemic mixture, enantomerically-enriched mixture, solvate, or prodrug of Formula I, is natural in origin, it is generally necessary to substantially purify and isolate such compound from the cellular debris of the organism that produced the compound. In this regard, in one embodiment, sweet green bell peppers (*Capsicum anuum* ssp. *grossum*) are sliced and pureed by hand or by mechanical means. The stems and/or seeds may be removed prior to the preparation of the puree. The puree may be filtered to a juice by conventional methodology, including, but not limited to, vacuum filtration. Highly non-polar compounds including, but not limited to chlorophylls and waxes may be removed from the juice by partitioning the juice between the hydrophilic aqueous phase and a non-polar solvent including, but not limited to, diethyl ether. The aqueous phase may be utilized for further separation, utilized as is, or subjected to trituration with short chain alcohols including, but not limited to methanol or ethanol to precipitate out compounds including, but not limited to, polypeptides and long chain carbohydrates.

The juice and/or triturated supernatant may be concentrated by conventional methodology such as rotary evaporation or freeze-drying or may be directly separated by column chromatography with sorbents (stationary phase) including, but not limited to, C-18 with fractions eluted with a gradient solvent (mobile phase) system including, but not limited to water:methanol and/or Sephadex LH-20 eluted with small chain alcohols including, but not limited to, pure methanol. Sub-fractions containing active analgesic compounds can be purified by methods including, but not limited to, HPLC or HPLC/mass spectrometry to yield pure isolates of active compounds.

Turning now to the following non-limiting Examples, the isolation, identification, and therapeutic effectiveness of compositions and compounds of the present invention are shown.

EXAMPLE 1

Analgesic Bioassay Protocol

A rat hindpaw assay was used to determine the therapeutic effectiveness of various extracts/compounds as analgesics in the present invention.

Sprague-Dawley rats (225-250 g, male) were anesthetized with urethane and placed on their sides on a disposable Chux pad. Both hindpaws for each rat were blackened with India ink which was allowed to dry for 10 minutes. An ELH projector lamp calibrated to a standard $mW/cm^2$ was used as a pain stimulus and was condensed into an area of 5×15 mm on each hindpaw and placed perpendicular to, and 72 mm from, each hindpaw.

Multiple baseline hindpaw withdrawal latency times were recorded (in seconds) for each medial and each lateral surface of each hindpaw. Subsequently, 100 µl of 1 µmolar capsaicin was applied with a pipette to cover one hindpaw of each animal and allowed to dry for 10 minutes, rendering the capsaicin-treated hindpaw hypersensitive to pain stimulus relative to the non-capsaicin treated hindpaw (and thereby decreasing the withdrawal latency period for the capsaicin-treated hindpaw relative to the non-treated hindpaw).

Both hindpaws were then re-blackened with India ink which was allowed to dry for 10 minutes, and hindpaw withdrawal latencies were recorded for both the capsaicin-treated and untreated hindpaws on both the medial and lateral aspects of both hindpaws at 20, 25 and 30 minutes. A significant drop in the withdrawal latency period was seen with the capsaicin-treated hindpaw, consistent with the reported effects of capsaicin as a pain hyper-sensitizing agent at general concentrations and dosages used in this bioassay. By contrast, only minor drops in the withdrawal latency periods of the untreated hindpaws was seen, and the effect that was observed is believed to be due to the central mechanism effect of capsaicin-treatment on the other hindpaw.

To determine the analgesic properties of each fraction, 100 μl of each fraction were applied to the capsaicin-treated hindpaw by pipette and permitted to dry (the untreated hindpaw was not treated with the fraction). Hindpaw withdrawal latencies were then recorded at 5, 20 and 30 minutes for both the capsaicin/fraction-treated hindpaw and the untreated hindpaw. An increase in the hindpaw withdrawal time was indicative of an analgesic effect by the applied fraction.

EXAMPLE 2

Isolation of Analgesic Compounds

Twelve (12) sweet green bell peppers (Capsicum anuum ssp. grossum) with stems, seeds and septae removed were put through a juice extractor (Panasonic model #MJ66PR) to yield 1200 ml liters of unfiltered juice. The juice was suction filtered with coarse filter paper through a Buchner funnel to yield 1.0 liters of filtered green pepper juice.

500 ml of filtered juice was partitioned with 500 ml of diethyl ether to remove waxes and chlorophylls. This partitioning was performed for a total of three times. Three layers were separated, the aqueous layer, the ether layer and an intermediate flocculent layer. Aliquots of each layer were tested by the Analgesic Bioassay (Example 1). Only the aqueous layer exhibited analgesic activity.

The aqueous layer was rotary evaporated at room temperature to 10 ml of a light brown gel which was triturated with two successive volumes of 100 ml methanol at room temperature to precipitate out long chain carbohydrates and polypeptides. The methanolic suspension was suction filtered with a Buchner funnel. The clear filtrate was dried down to 1 ml of a viscous amber liquid in a rotary evaporator at 40° C.

1.0 g of the concentrated methanolic extract was fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step.

Aliquots of each fraction tested by the Analgesic Bioassay (Example 1) demonstrated analgesic activity concentrated in fraction E (the 80% methanol:water fraction). Bioassay testing further demonstrated retention of bioactivity on heating of active samples to 45° C. and on acidifying the same sample to pH 4.4. Analgesic activity was lost on alkalinization to pH 8.4. The analgesic effect of analgesic fractions was not lost on administration of naloxone, a narcotic antagonist, to the test animals, which was indicative that the induced analgesia was not from a narcotic entity (Table 1). Fraction E showed increasing analgesic effect over time even after naloxone administration.

TABLE 1

Analgesic Effect of Extract Fraction E

| Fraction | n | Avg. Baseline | Avg. Post-Cap | Avg. Post-Fract | Avg. Post-Naloxone |
|---|---|---|---|---|---|
| E (80% MeOH) | 2 | 12.65 | 5.38 | 18.05 | 15.36 |
| SEM | | 0.48 | 0.42 | 4.02 | 0.82 |
| Control | 2 | 12.58 | 10.09 | 10.41 | N/A |
| SEM | | 0.32 | 0.34 | 1.84 | N/A |

EXAMPLE 3

Sub-fractionation of Fraction E 1.0 g of the original concentrated methanolic extract was fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step.

1.0 g of the concentrated 80% methanol fraction was re-fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step. The 80% methanol fractions were collected in 5 ml aliquots labeled EEa, EEb, EEc and EEd. All of these sub-fractions exhibited analgesic activity with the greatest analgesic activity noted in fraction EEa.

EXAMPLE 4

Identification of Sub-fraction BMBW-M40i 3000 mL of the juice of sweet green bell peppers (Capsicum anuum ssp. grossum) exhibiting strong analgesic activity by the Analgesic Bioassay (Example 1) was partitioned with 1000 ml of diethyl ether. This partitioning was performed for a total of three times. The aqueous layer was filtered, concentrated and lyophilized in vacuo at 35.8° C. to yield 135.2 g of brown extract.

21.0 g of the lyophilized extract was fractionated by column chromatography with a stationary phase of C-18 reverse phase silica gel (40 μm; J. T. Baker, Phillipsburg, N.J.). Fractions were eluted with a gradient solvent system of 0:1 to 1:0 methanol/water (mobile phase) in increments of 10% methanol per step. Thirteen fractions were obtained and compared by thin layer chromatography to known bioactive fraction EEa (see Example 3).

Bioassays were performed as described above on fractions eluted with 30%-80% methanol based on matching thin layer chromatograms to standard EEa. Fractions adjacent to these matching fractions were also bioassayed. Results of bioassay testing (latencies in seconds and corresponding standard errors of the mean (SEM) were recorded for fractions obtained throughout the isolation and purification procedures described. Sub-fractionations were guided by both 1) bioassay testing, as described above, and 2) comparing thin layer chromatograms of fractions and sub-fractions obtained as described herein to fraction EEa (see Example 3). Based on bioassayed analgesic activity, aliquots of the 40% fraction (BMBW-M40, total weight 99.8 mg) and the 60% fraction (BMBW-M60, total weight 102.1 mg) were further sub-fractionated.

66.0 mg of BMBW-M40 was sub-fractionated by column chromatography with a stationary phase of Sephadex LH-20 (10.0 g, 25-100 μm; Pharmacia Fine Chemicals, Piscataway, N.J.). Sub-fractions were eluted with a solvent system of pure methanol. Sub-fractions were combined based on HPLC analyses to yield twelve sub-fractions.

Bioassays were performed as described above on all twelve fractions. Based on its assayed bioactivity, fraction BMBW-M40i (total weight 3.6 mg) was further sub-sub-fractionated.

70.5 mg of BMBW-M60 was sub-fractionated by column chromatography with a stationary phase of Sephadex LH-20 (10.0 g, 25-100 μm; Pharmacia Fine Chemicals, Piscataway, N.J.). Sub-fractions were eluted with a solvent system of pure methanol. Sub-fractions were combined based on HPLC analyses to yield sixteen sub-fractions. In bioassays performed as described above, all of the BMBW-M60 sub-fractions failed to demonstrate the significant retention of analgesic activity.

Sub-fraction BMBW-M40i was analyzed by HPLC analyses on a Waters 2690 separation module equipped with a Waters 996 photodiode array detector and Empower software using a Phenomenex Aqua $C_{18}$ column (4.6×250 mm, 5 μm) and a HPLC gradient program (Table 2), column at room temperature, 65 min run time.

TABLE 2

HPLC Analysis of Sub-fraction BMBW-M40i

| Time (min) | Flow (ml/min) | Water (%) | Methanol (%) | Curve |
|---|---|---|---|---|
| 0.00 | 1.00 | 95.0 | 5.0 | Linear-6 |
| 10.00 | 1.00 | 50.0 | 50.0 | Linear-6 |
| 15.00 | 1.00 | 50.0 | 50.0 | Linear-6 |
| 50.00 | 1.00 | 5.0 | 95.0 | Linear-5 |
| 65.00 | 1.00 | 95.0 | 5.0 | Linear-6 |

Nine peaks were identified and labeled BMBW-M40i1, 2, 3, 4,A, 5,B, 6, 7 and a broad bimodal peak between 45 and 55 minutes labeled 8 and 9 (see FIG. 1, which shows HPLC chromatograms and UV spectra of BMBW-M40i peaks). The UV spectra in FIG. 1 indicated that peaks 1, 2, 3, 4 and 7 were likely to have aromatic rings and peaks A, B, 5, and 6 were unlikely to have aromatic rings.

Figure 2:
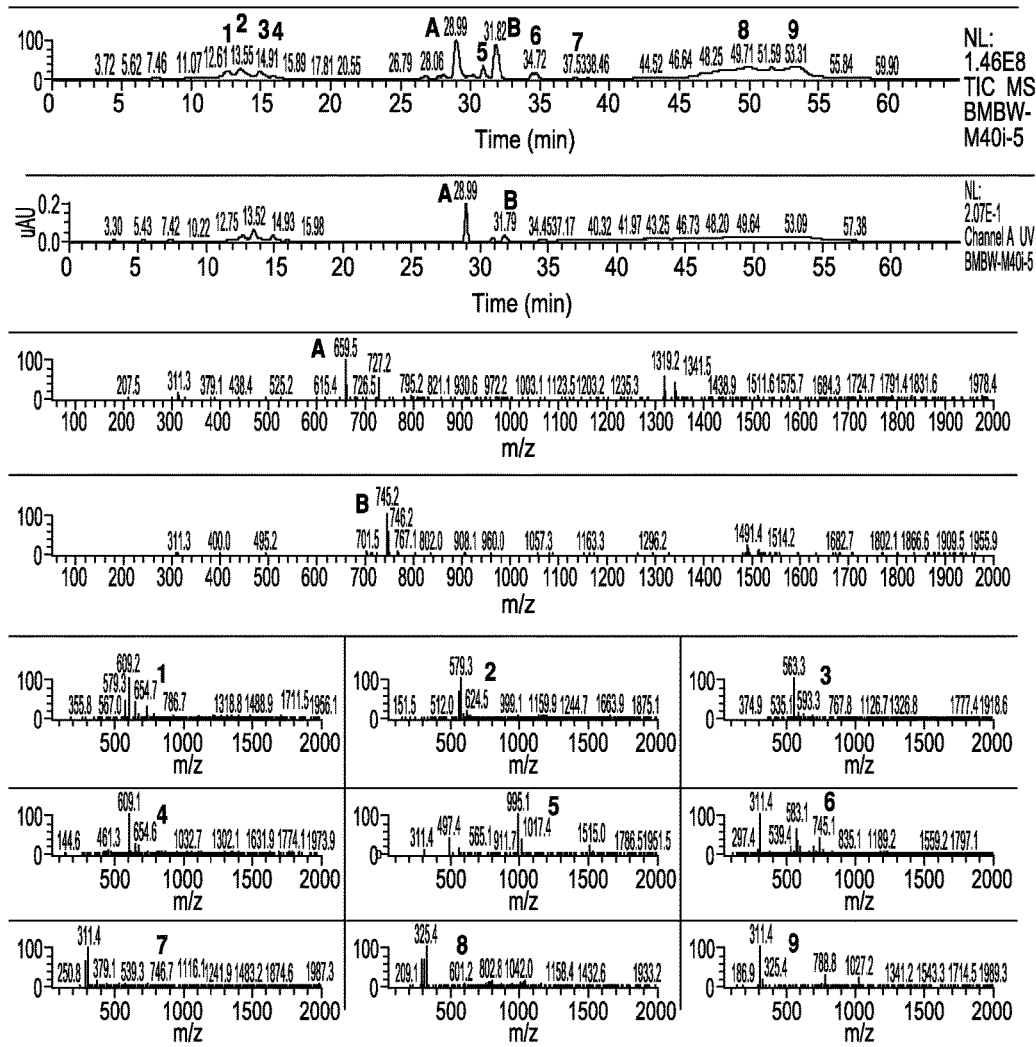
FIG. 2 shows TIC, UV (221 nm) and negative ESIMS spectra of the peaks of fraction BMBW-M40i.

Sub-fraction BMBW-M40i was subjected to HPLC-MS analysis. 1.8 mg of BMBW-M40i was dissolved in 1.0 ml methanol. 20 μL of this solution was diluted with 100 μL of methanol and was analyzed by negative electrospray ionization mass spectrometry (ESIMS) with a ThermoFinnigan LCQ instrument (San Jose, Calif.) equipped with Xcalibur software. The sample was introduced by a Waters 2690 separation module, equipped with a Waters 2487 dual λ absorbance detector. The capillary voltage was set at 10 V with a spray voltage of 4.5 kV, tube lens offset of 0 V and capillary temperature of 230° C. The sheath gas and auxiliary gas were both Nitrogen with flow rates of 80 and 30, respectively. Results of this negative ESIMS are shown in FIG. 2.

HPLC/MS by positive ESIMS was performed on BMBW-M40i on an Agilent Technologies 1100 Series LC/MSD model G1946D using electrospray ionization. Ionization was carried out with a drying gas temperature of 200° C., a nebulizer pressure of 40 psi and a flow rate of 13 L/min. The mass range scanned was between 140 and 1500 amu with fragmentor values of 70 volts in both positive and negative mode. The capillary was set to 4000 volts. Prior to mass spectral analysis the sample was analyzed on an Agilent Technologies 1100 analytical HPLC using a Zorbax Eclipse XDB-C18 2.1 mm×150 mm 5-micron column (part number 993700-902) operated at a temperature of 36° C. The mobile phase consisted of 0.1% (v/v) formic acid and 50 uM ammonium acetate in water (Eluent A) and of 0.1% (v/v) formic acid and 50 uM ammonium acetate in acetonitrile (Eluent B) according to the gradient in Table 3.

TABLE 3

HPLC Analysis of Sub-fraction BMBW-M40i

| Time (min) | Flow (ml/min) | Eluent A (%) | Eluent B (%) | Curve |
|---|---|---|---|---|
| 0.00 | 0.4 | 90.0 | 10.0 | Linear |
| 2.00 | 0.4 | 90.0 | 10.0 | Linear |
| 60.00 | 0.4 | 55.0 | 45.0 | Linear |
| 80.00 | 0.4 | 0.0 | 100.0 | Linear |
| 85.00 | 0.4 | 0.0 | 100.0 | Linear |

The injection volume was 25 μL. Simultaneous monitoring was performed at 230 nm and 260 nm. Spectra were recorded from 200 to 900 nm. Data was processed using Agilent's Chemstation software.

Mass spectral data by positive ESIMS revealed the primary constituents of BMBW-M40i to have m/z 698 ($M^+NH_4^+$), m/z 764 ($M^+NH_4^+$), m/z 516 ($M^+NH_4^+$) with it corresponding m/z 1014 ($2M^+NH_4^+$) and a small peak for m/z 602 ($M^+NH_4^+$).

1.6 mg of BMBW-M40i was sub-sub-fractionated by analytic HPLC on a Waters 690 separation module equipped with a Waters 996 photodiode array detector and Empower software using a 250×4.6 mm i.d., 5 μm, Aqua $C_{18}$ column (Phenomenex, Torrance, Calif.). An HPLC gradient program (see Table 1) resulted in ten sub-sub-fractions, BMBW-M40i-1, 2, 3, 4,A, 5,B, 6, 7 and 8, which were all subjected to the Analgesic Bioassay (Example 1). Results from various fractions: BMBW-M40i-5 ("Fraction i5") and the inactive fraction: BMBW-M40i-A ("Fraction iA") are summarized in Table 4. Latencies are recorded in seconds along with their corresponding standard errors of the mean (SEM).

TABLE 4

Analgesic Bioassay Results: Sub-fractions i5 and iA

| | n | Avg: All Baselines | Avg.: Cap. @ 20 min | Avg.: Cap. @ 25 min | Avg.: Cap. @ 30 min | Avg.: All Capsaicin | Avg.: Fract. @ 5 min | Avg.: Fract. @ 20 min | Avg.: Fract. @ 30 min |
|---|---|---|---|---|---|---|---|---|---|
| Fraction i5 | 5 | 15.78 | 10.62 | 7.95 | 7.99 | 8.8533333 | 18.01 | 15.24 | 12.21 |
| SEM | | 0.6334797 | 0.7133333 | 0.3763125 | 0.4942896 | 0.3826025 | 0.9902244 | 1.8288551 | 1.6423188 |
| Control | 5 | 16.22 | 11.28 | 11.66 | 11.48 | 11.473333 | 12.17 | 12.33 | 11.63 |
| SEM | | 0.6334797 | 0.6371464 | 1.2089665 | 1.3431969 | 0.6169807 | 1.2020399 | 0.9673618 | 1.0826972 |
| Fraction iA | 5 | 10.963333 | 6.88 | 6.46 | 6.63 | 6.6566667 | 12.34 | 7.83 | 6.1 |
| SEM | | 0.6559311 | 1.1114355 | 0.7453858 | 0.6690042 | 0.4822763 | 1.9743466 | 1.7967285 | 0.6489307 |
| Control | 5 | 12.356667 | 13.41 | 10.04 | 11.83 | 11.76 | 10.99 | 11.68 | 11.7 |
| SEM | | 0.6559311 | 1.492831 | 1.3648932 | 1.4038875 | 0.8321638 | 1.5603027 | 1.2797396 | 1.8506455 |

Five animals were tested for the analgesic effect of each fraction. Baseline hindpaw withdrawal times were measured (i.e., prior to any treatments), after which capsaicin was administered to one of the two hindpaws of each animal (according to the protocol set forth in Example 1), and then the fraction was administered to the capsaicin-treated hindpaw of each animal. As shown in Table 4, for Fraction i5, the average baseline withdrawal time was 15.78 seconds, which decreased to 10.62, 7.95 and 7.99 seconds at 20 mins, 25 mins and 30 mins post-capsaicin treatment, respectively; consistent with capsaicin's known hyper-sensitizing effect to pain at the administered dose. Fraction i5 was then added to the capsaicin-treated hindpaw, increasing the withdrawal latency period to 18.01, 15.24 and 12.21 seconds at 5 mins, 20 mins and 30 mins post-fraction treatment, respectively; evidencing a strong analgesic effect by Fraction i5. The untreated control hindpaw did not show any significant change in withdrawal time over the same period.

Latencies after application of Fraction i5 at 20 minutes as compared to the 30 minute capsaicin latencies were highly statistically significant (by single factor ANOVA) with a of P-value of 0.001235035. The results with Fraction iA were not statistically significant with a P-value of 0.539236411.

Figure 3:
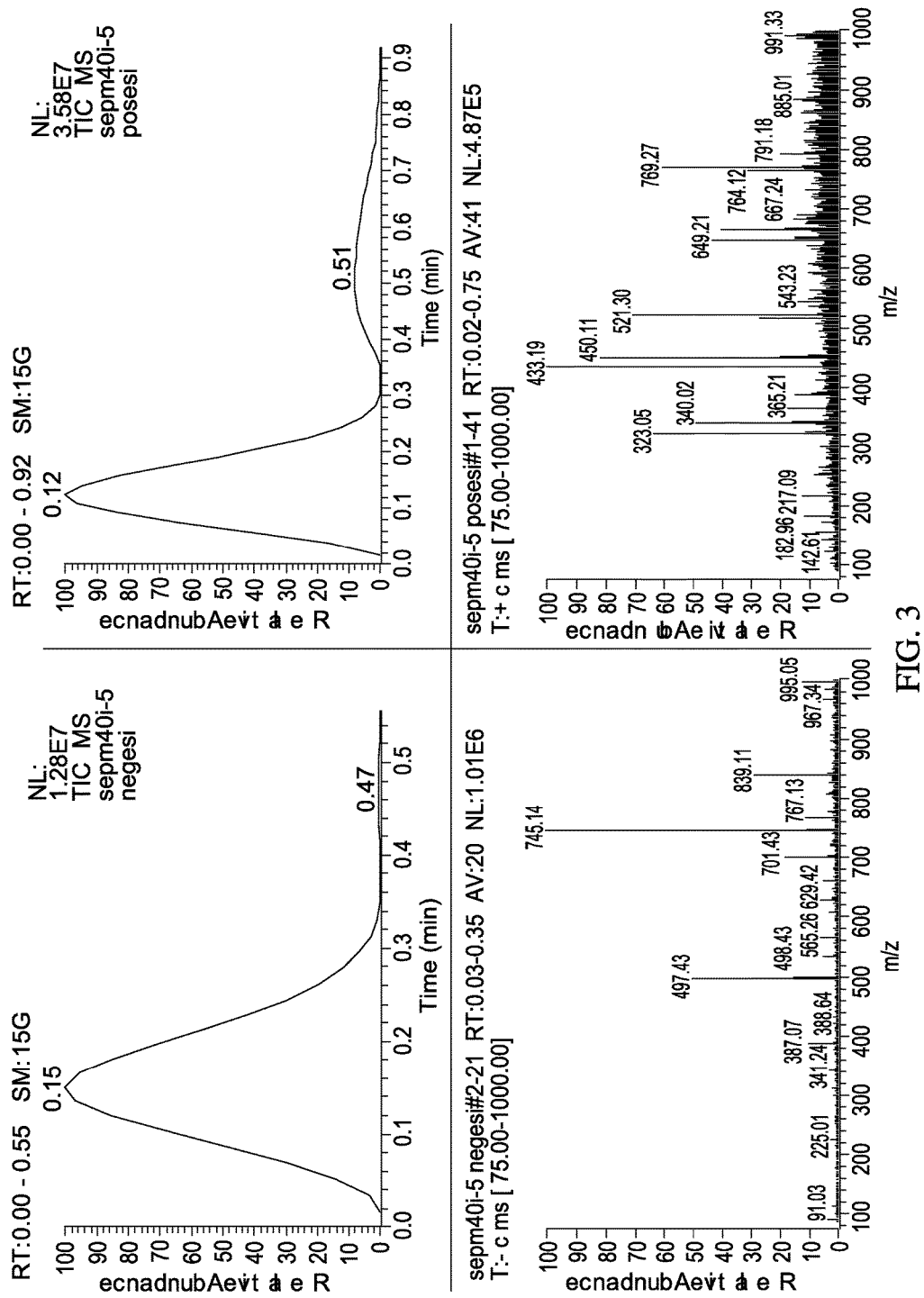
FIG. 3 shows ESIMS results of fraction BMBW-M40i-5.
Figure 5:
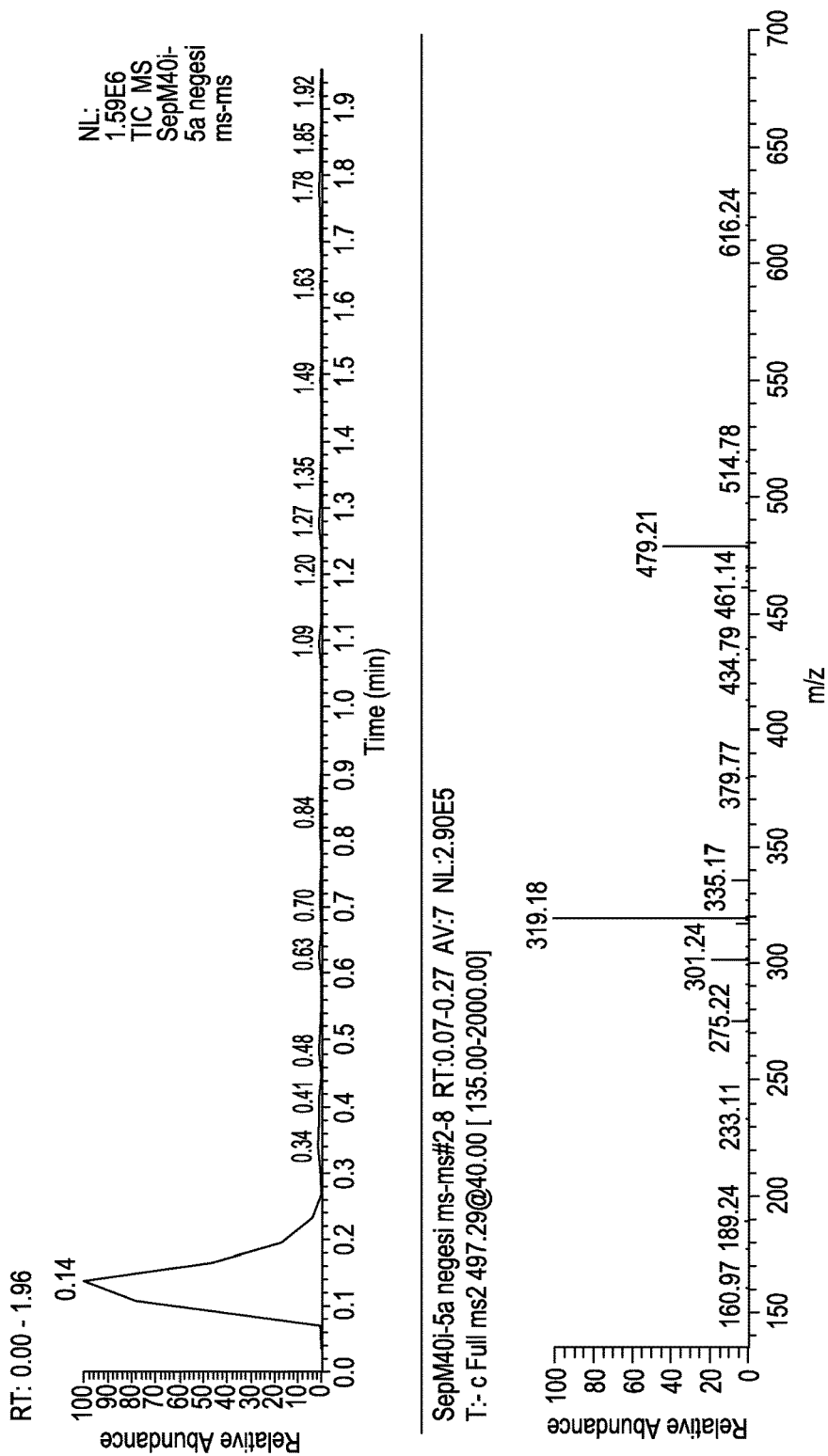
FIG. 5 shows negative ESI MS/MS spectra of ion with m/z 497.43 from fraction BMBW-M40i-5.

Sub-sub-fraction BMBW-M40i-5 (FIG. 5) was tested by both negative and positive ESIMS by direct injection. Samples were dissolved in MeOH and were introduced by a Waters 2690 separations module using an isocratic solvent system of 50:50 MeCN/$H_2O$, a flow rate of 0.3 ml/min. The capillary voltage was 10 V, the spray voltage was 4.5 kV, and the tube lens offset was 0 V. The capillary temperature was 230° C. The sheath gas and auxiliary gas were both nitrogen with flow rates of 80 and 30, respectively. Results are shown in FIG. 3.

Sub-sub-fraction BMBW-M40i-5 consisted primarily of negative ESIMS m/z 497.43 and 745.14. Negative ESIMS m/z 745.14, was the primary constituent of BMBW-M40i-B, which had been shown to have no analgesic activity by bioassay with the Analgesic Bioassay (Example 1).

Figure 4:
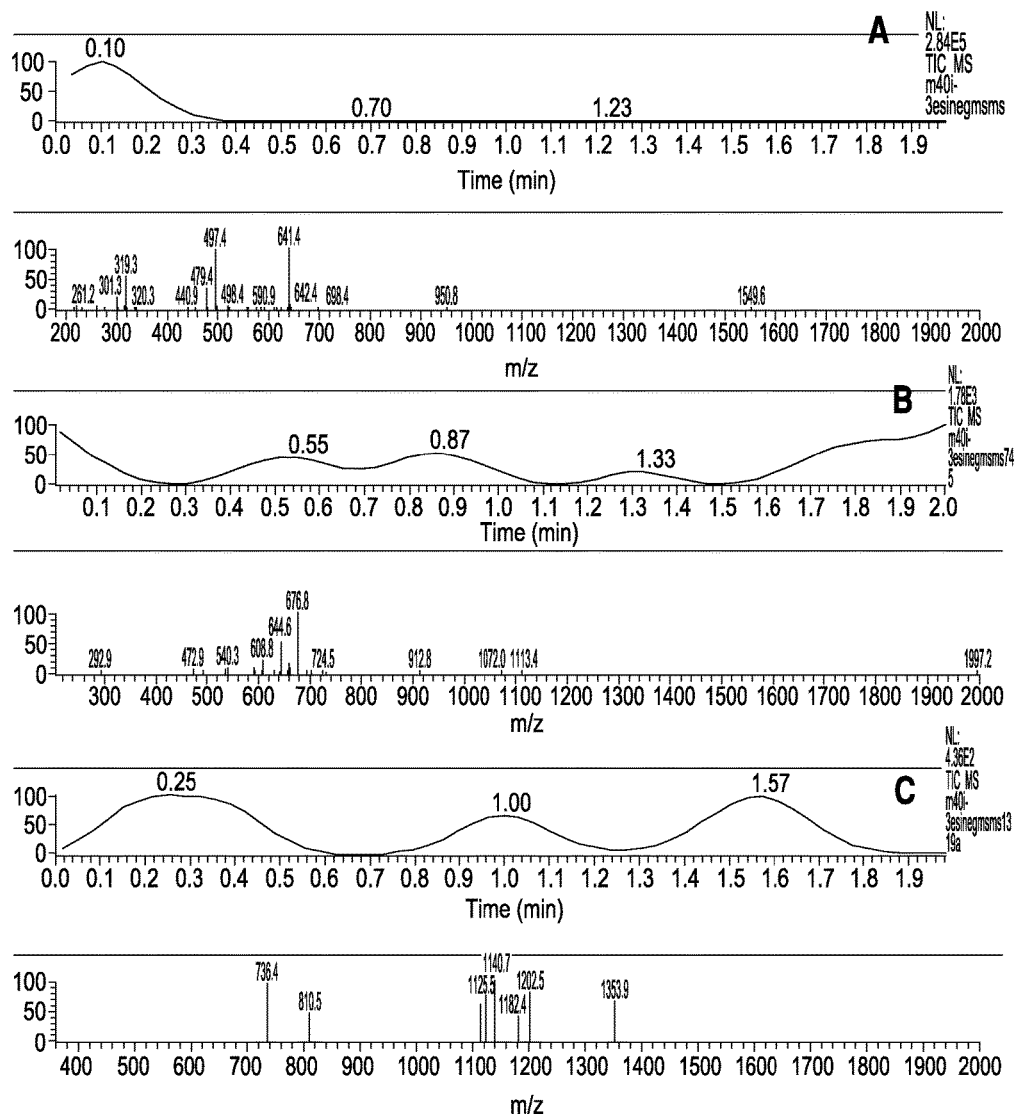
FIG. 4 shows TIC and negative ESI MS/MS spectra of ions with m/z 659.45 from fraction BMBW-M40iA (A), m/z 745.19 (B), and m/z 1319.17 (C).

The ions with m/z 659.45 (A), 745.19 (B), and 1319.17 (C) by negative ESIMS were selected as parent ions for MS/MS experiments, with results shown in FIG. 4. MS/MS was also performed on the negative ESIMS parent ion with n/z 497.43 from sub-sub-fraction BMBW-M40i-5, with results shown in FIG. 5. From this MS/MS analysis, it was apparent that the parent ion m/z 659.45 yields fragments with m/z 497.4, 319.3 and 301.3, whereas the parent ion m/z 479.21 also yields fragments with m/z 319.18 and 301.24. BMBW-M40i-A, with its primary constituent with negative ESIMS m/z 659.45, had not exhibited analgesic activity, whereas BMBW-M40i-5 exhibited strong analgesic activity. The difference between negative ESIMS m/z 659.45 and m/z 497.43 is 162.02, suggesting a difference of a hexose glycoside moiety.

The positive ESIMS data for fractions E, EEA, BMBW-M40i and BMBW-M40i-5 were searched for the ions present in fraction BMBW-M40i m/z ($M^+NH_4^+$) 678, 764, 516 and 602. Areas under the peaks for these respective ions were integrated. Significant bioactivity correlated with a high concentration of m/z 516 (corresponding to the diterpene monoglycoside) relative to m/z 678 (the corresponding diterpene diglycoside).

High resolution MS was performed by positive ESI on a Micromass AutoSpec instrument using electrospray ionization mode with $M^+(Na^+)$ on ions yielding m/z 683.3256 (mw=660) and m/z 521.2825 (mw=498). Average isotopic mass intensity distributions for these ions are summarized in Table 5.

TABLE 5

High Res MS Results, Compounds with MW = 660 and MW = 498

| Carbon Isotope | m/z 521 | m/z 683 |
| --- | --- | --- |
| C12 | 100.0% | 100.0% |
| C13 | 27.5% | 38.8% |
| C14 | 6.0% | 11.9% |

The best fit for calculated isotopic mass intensity distributions from tables of generated possible molecular formulae for the high-resolution MS data for the hetero-ions: C, H, N, O and Na are summarized in Table 6.

TABLE 6

Determination of Compound Formulas from MS Results

| m/z ($M^+Na^+$) | C | H | N | O | Na | Mass | Diff | ppm |
| --- | --- | --- | --- | --- | --- | --- | --- | --- |
| 683.3256 | 32 | 52 | 0 | 14 | 1 | 683.3254 | 0.0001 | 0.1 |
| 683.3256 | 33 | 48 | 4 | 10 | 1 | 683.3268 | −0.0012 | −1.8 |
| 521.2825 | 25 | 42 | 2 | 8 | 1 | 521.2839 | −0.0014 | −2.7 |
| 521.2825 | 26 | 42 | 0 | 9 | 1 | 521.2726 | 0.0098 | 18.8 |

Only $C_{26}H_{42}O_9$ and $C_{32}H_{52}O_{14}$ fit the constraints of a low difference between measured and calculated high resolution molecular weights, the best fit to the measured isotopic mass intensity distributions and differing from each other by 162 (a hexose glycoside moiety).

EXAMPLE 5

Compound Identification 1D and 2D NMR experiments were conducted on the two compounds identified in Example 4, the first compound wherein m/z 683.3256 (mw=660) (hereinafter "Compound-660") and the second compound wherein m/z 521.2825 (mw=498) (hereinafter "Compound-498").

Figure 6:
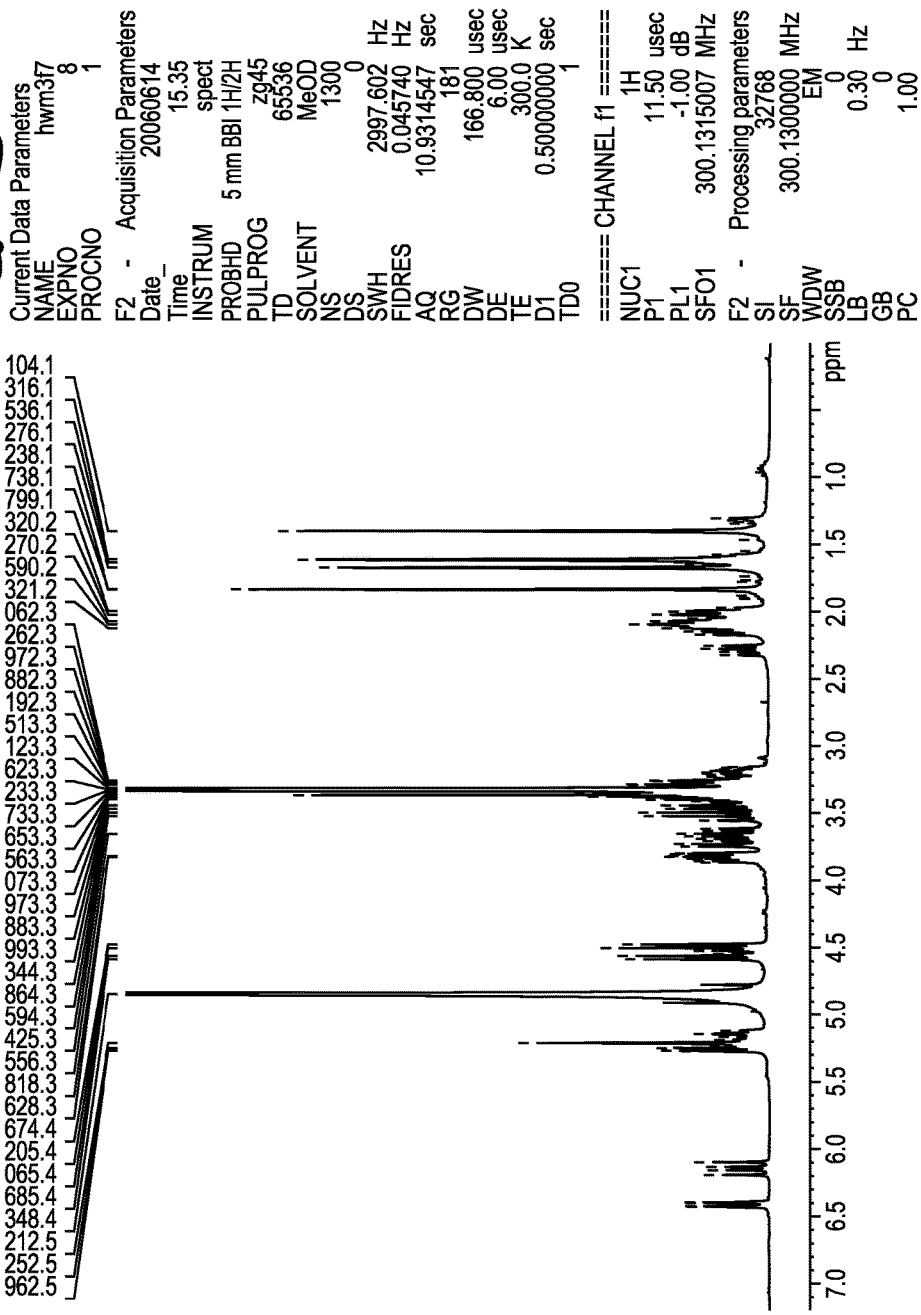
FIG. 6 shows 1D $^1$H-NMR spectra of Compound-660.
Figure 7:
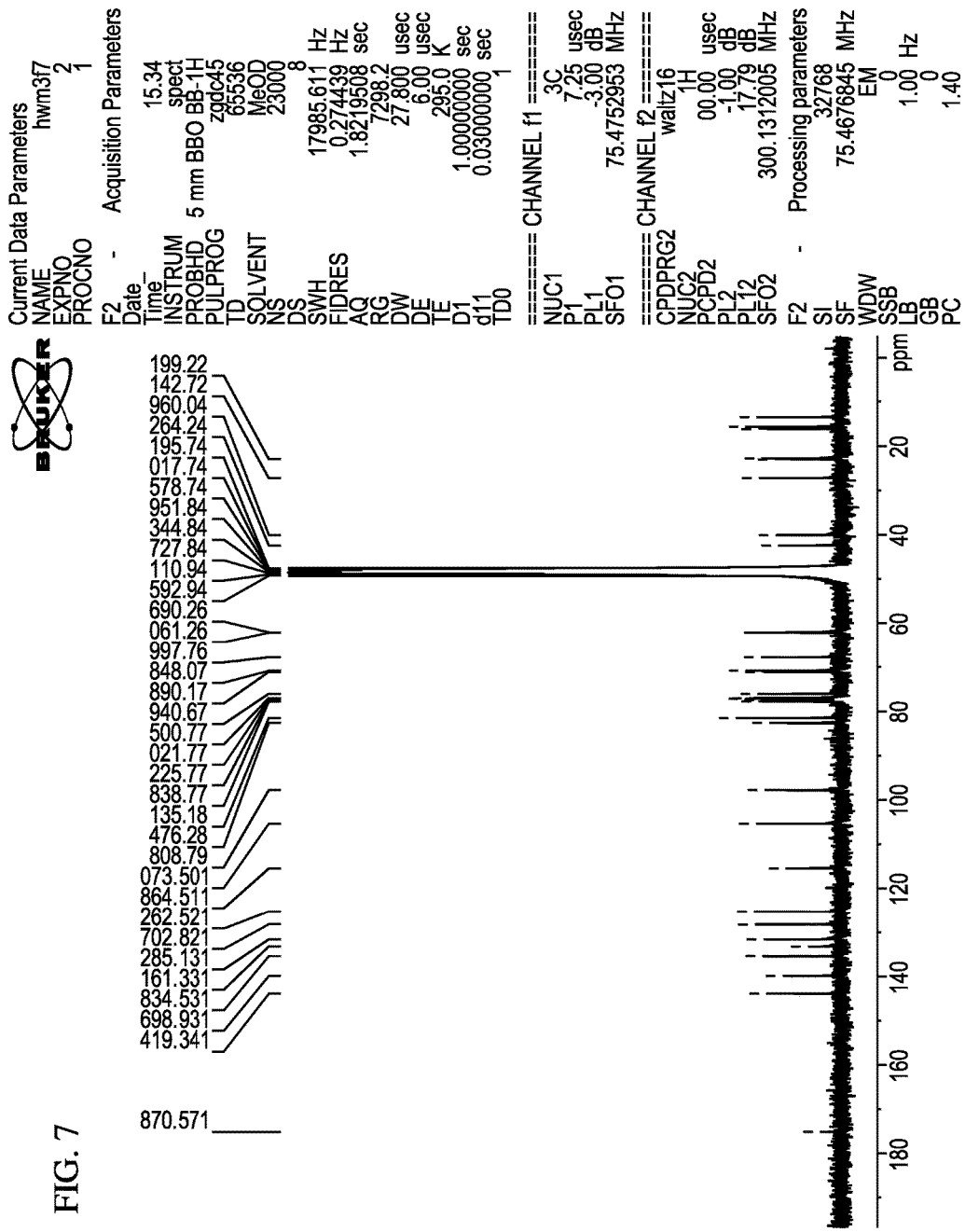
FIG. 7 shows 1D $^{13}$C NMR spectra of Compound-660.
Figure 8:
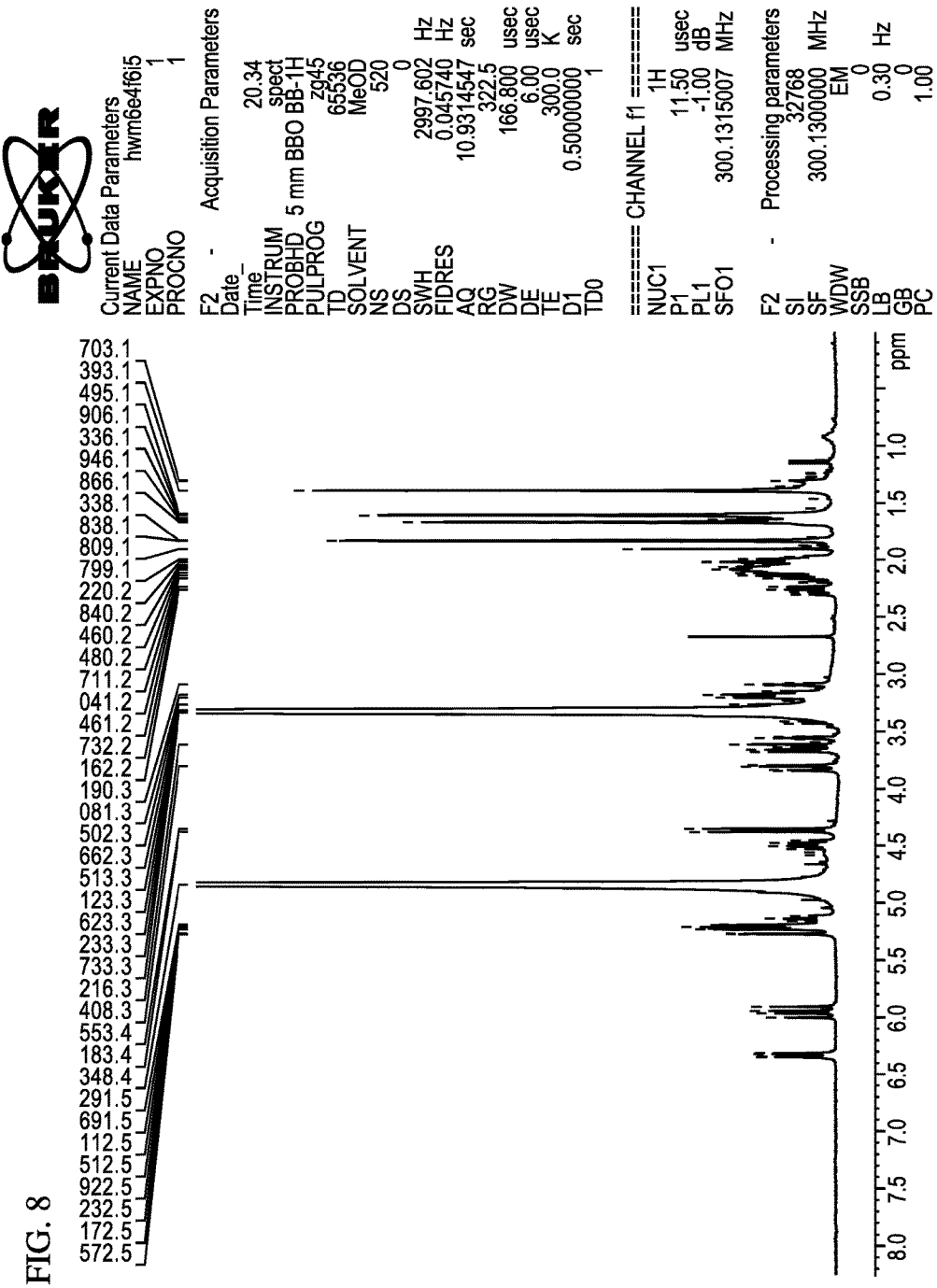
FIG. 8 shows 1D $^1$H-NMR spectra of Compound-498.
Figure 9:
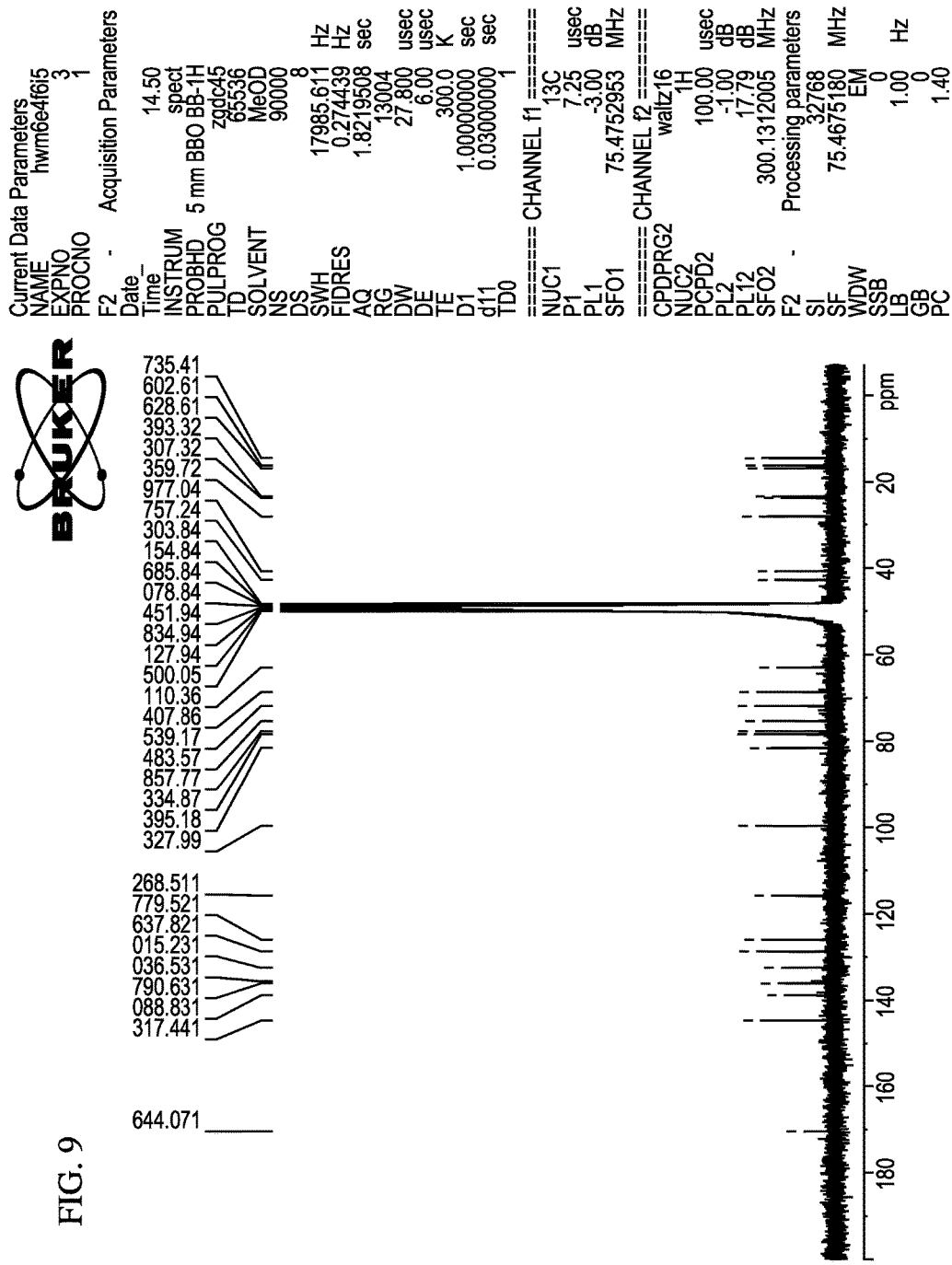
FIG. 9 shows 1D $^{13}$C NMR spectra of Compound-498.

1D $^1H$, $^{13}C$ NMR and 2D NMR experiments were run on a Bruker Avance AV-300 spectrometer at 300 MHz ($^1H$) and 75 MHz ($^{13}C$). The 2D experiments edited-HSQC, $^1H$-$^1H$ COSY, NOESY, TOCSY, and HMBC were acquired using standard Bruker pulse sequences. Compound-660 and compound-498 were measured in Methanol-$d_4$. FIGS. 6 and 7 show the 1D $^1H$-NMR and $^{13}C$ NMR spectra of Compound-660, respectively. FIGS. 8 and 9 show the 1D $^1H$-NMR and $^{13}C$ NMR spectra of Compound-498, respectively.

LC-MS and NMR analyses of Compound-660 and Compound-498 indicated that they were of very high purities. Therefore, excellent NMR spectra of these two compounds were obtained, despite the small amounts of each pure compound. High purity was also important for bioassay specificity.

Figure 10:
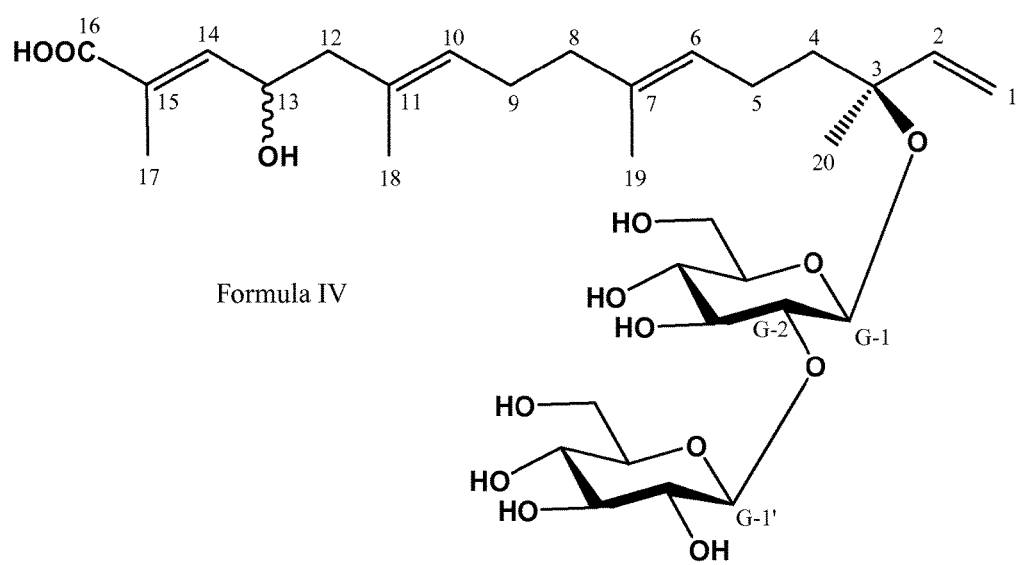
FIG. 10 shows the structure of Compound-660 (Formula IV).
Figure 11:
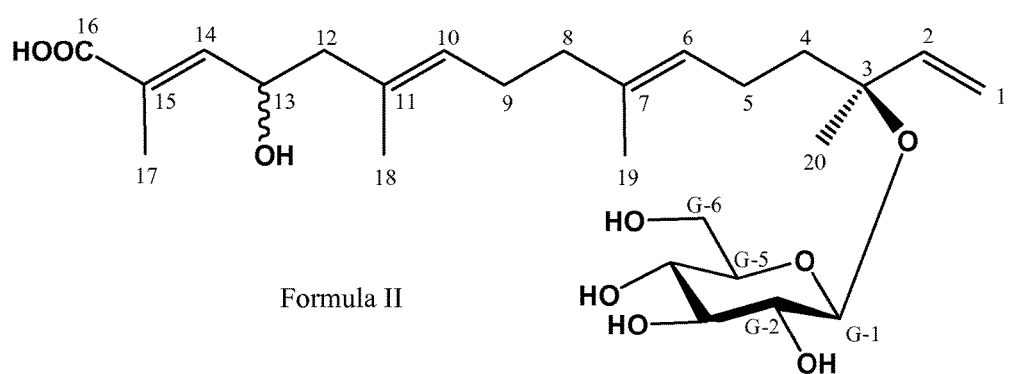
FIG. 11 shows the structure of Compound-498 (Formula II).

The structural elucidation of the two compounds has been performed on the basis of spectroscopic methods. Interpretation of 1D and 2D NMR spectra of these two compounds and comparison of their NMR data with those of literature data (Izumitani, Y.; Yahara, S.; Nohara, T.; Novel acyclic diterpene glycosides, capsianoside A-F and I-V from *Capsicum* Plant (Solanaceous studies. XVI). *Chem. Pharm. Bull.* 1990, 38: 1299-1307) resulted in the identification of Compound-660 and Compound-498 as capsianoside I, and 14-(beta-D-glucopyranosyloxy)-4-hydroxy-2,6,10,14-tetramethyl-2,6,10,15-hexadecatetraenoic acid [4R-(2E,4R*,6E,10E,14S*)], respectively. Their structures are shown in FIGS. 10 and 11, respectively. As seen by their structures, neither Compound 498 nor Compound 660 is a capsaicinoid.

Bioassays of pure Compound-498 and pure Compound-660 were performed according to the Analgesic Bioassay (Example 1) and are summarized in Table 7.

TABLE 7

Analgesic Bioassay Results: Compounds 498 and 660

| Compound | n | Avg. All Baselines | Avg. Cap. @ 20 min | Avg. Cap. @ 25 min | Avg. Cap. @ 30 min | Avg. All Capsaicin | Avg. Cmpd. @ 5 min | Avg. Cmpd. @ 20 min | Avg. Cmpd @ 30 min |
|---|---|---|---|---|---|---|---|---|---|
| Pure 498 (0.27 mg) | 5 | 10.76667 | 7.4 | 7.9555556 | 5.4 | 6.9 | 13.6 | 9.4 | 8.1 |
| SEM | | 0.5689 | 0.8032918 | 0.5984032 | 0.5822477 | 0.4289881 | 0.6795357 | 0.8901745 | 0.9969552 |
| Control | 5 | 11.4 | 11.6 | 8.9 | 8.9 | 9.8 | 8.9 | 10.3 | 11.7 |
| SEM | | 0.667116 | 1.0950444 | 0.6883232 | 0.5454458 | 0.5106393 | 0.6627887 | 1.0082989 | 1.0496825 |
| Pure 660 (0.33 mg) | 5 | 9.5 | 9.5 | 6.4 | 5.9 | 7.3 | 10.5 | 9.6 | 6.5 |
| SEM | | 0.65701 | 1.676192 | 1.210731 | 0.601171 | 0.762421 | 1.661325 | 1.519802 | 0.86127 |
| Control | 5 | 11.2 | 11.3 | 9.4 | 8.5 | 9.7 | 9.5 | 10 | 9.3 |
| SEM | | 0.641904 | 1.003599 | 0.762132 | 0.674792 | 0.508637 | 0.849215 | 1.068623 | 1.132235 |

Five animals were tested for the analgesic effect of each compound. Baseline hindpaw withdrawal times were measured (i.e., prior to any treatments), after which capsaicin was administered to one of the two hindpaws of each animal (according to the protocol set forth in Example 1), and then the compound was administered to the capsaicin-treated hindpaw of each animal. As shown in Table 7, for Compound 498, the average baseline withdrawal time was 10.76667 seconds, which decreased to 7.4, 7.9555556 and 5.4 seconds at 20 mins, 25 mins and 30 mins post-capsaicin treatment, respectively; consistent with capsaicin's known hyper-sensitizing effect to pain at the administered dose. Compound 498 was then added to the capsaicin-treated hindpaw, increasing the withdrawal latency period to 13.6, 9.4 and 8.1 seconds at 5 mins, 20 mins and 30 mins post-compound treatment, respectively; evidencing a strong analgesic effect by Compound 498. The untreated control hindpaw did not show any significant change in withdrawal time over the same period.

Latencies after application of the pure Compound-498 at 20 minutes as compared to the 30 minute capsaicin latencies were highly statistically significant (by single factor ANOVA) with a of P-value of 0.001788293. The results with the pure Compound-660 had a less significant P-value of 0.042369157.

In this Analgesic Bioassay pain model, analgesia resulting from the compounds of the present invention was comparable to 0.1 mg/kg of systemic morphine.

EXAMPLE 5

Inflammation Bioassay Protocol

A mouse air pouch assay was used to determine the therapeutic effectiveness of various extracts/compounds as anti-inflammatory agents in the present invention.

To induce air pouches, 10-15 week old mice were injected subcutaneously on the back with 3 ml of air.

On day 2, the pouches were reinflated with 1.5 m. of air.

On day 6, inflammation was induced by injecting 1 ml of a suspension of carrageenan (2% weight/volume in calcium-free and magnesium-free phosphate buffered saline (PBS) solution) into the air pouch.

100 µL of solution including test compounds were injected with the carrageenan (additional 100 µL of PBS were injected into the controls).

After 4 hours, the mice were sacrificed by including $CO_2$ narcosis, the pouches were flushed with 2 ml of PBS, and exudates were harvested.

Exudates were diluted 1:1 with 0.015% methylene blue in PBS.

White blood cells were counted in a standard hemocytometer chamber (American Optical, Buffalo, N.Y.).

EXAMPLE 6

Inflammation Bioassay Results

Compound 660 (Formula TV) was assayed for anti-inflammatory activity according to the Inflammation Bioassay Protocol (Example 5). With the carrageenan injection, five mice received injections of 100 µL of test solution containing Compound 660, and eleven control mice received injections of 100 µL of PBS. The exudates were harvested from the air pouches and white blood cells counted, the results of which are set forth in Table 8 (Control) and Table 9 (Compound 660).

TABLE 8

Inflammation Bioassay Results: Controls

| Mouse Number | Volume (ml) | Cell Count (4 chambers) | | | Average Count | Dilution Factor | Cells/ml | Cells ($10^6$/ml) | Average Cells ($10^6$/ml) |
|---|---|---|---|---|---|---|---|---|---|
| 1 | 2 | 98 | 103 | 145 | 86 | 108.00 | 216 | 2.16E+06 | 2.16 | |
| 2 | 2 | 80 | 93 | 100 | 78 | 87.75 | 175.5 | 1.76E+06 | 1.76 | |
| 3 | 2 | 68 | 84 | 78 | 110 | 85.00 | 170 | 1.70E+06 | 1.70 | |
| 4 | 2 | 56 | 100 | 72 | 95 | 80.75 | 161.5 | 1.62E+06 | 1.62 | |
| 5 | 2 | 167 | 65 | 74 | 111 | 104.25 | 208.5 | 2.09E+06 | 2.09 | |
| 9 | 3 | 82 | 98 | 79 | 104 | 90.75 | 272.25 | 2.72E+06 | 2.72 | 2.67 |
| 10 | 3 | 63 | 95 | 86 | 119 | 90.75 | 272.25 | 2.72E+06 | 2.72 | |
| 14 | 3.5 | 150 | 108 | 48 | 67 | 93.25 | 326.375 | 3.26E+06 | 3.26 | |
| 15 | 3.5 | 75 | 120 | 132 | 128 | 113.75 | 398.125 | 3.98E+06 | 3.98 | |

TABLE 8-continued

Inflammation Bioassay Results: Controls

| Mouse Number | Volume (ml) | Cell Count (4 chambers) | | | | Average Count | Dilution Factor | Cells/ml | Cells ($10^6$/ml) | Average Cells ($10^6$/ml) |
|---|---|---|---|---|---|---|---|---|---|---|
| 16 | 2.5 | 259 | 156 | 125 | 234 | 193.0 | 483.75 | 4.84E+06 | 4.84 | |
| 17 | 2 | 130 | 86 | 95 | 199 | 127.50 | 255 | 2.55E+06 | 2.55 | |

TABLE 9

Inflammation Bioassay Results: Compound 660

| Mouse Number | Volume (ml) | Cell Count (4 chambers) | | | | Average Count | Dilution Factor | Cells/ml | Cells ($10^6$/ml) | Average Cells ($10^6$/ml) | P-value |
|---|---|---|---|---|---|---|---|---|---|---|---|
| 11 | 1 | 35 | 27 | 23 | 44 | 32.25 | 32.25 | 3.23E+05 | 0.32 | | |
| 12 | 2.5 | 45 | 48 | 64 | 18 | 43.75 | 109.375 | 1.09E+06 | 1.09 | | |
| 13 | 2.5 | 101 | 82 | 96 | 120 | 99.75 | 249.375 | 2.49E+06 | 2.49 | 1.54 | 0.05255485 |
| 20 | 2 | 44 | 82 | 57 | 76 | 64.75 | 129.5 | 1.30E+06 | 1.30 | | |
| 21 | 1.5 | 152 | 199 | 108 | 204 | 165.75 | 248.625 | 2.49E+06 | 2.49 | | |

As shown, the average white cell volume ($10^6$ cells per ml) in aliquots from mice treated with test Compound 660 is 1.54 compared to 2.67 in the control mice, establishing the efficacy of Compound 660 as an anti-inflammatory agent (P-value of 0.05255485). The anti-inflammatory effects of Compound 660 are comparable to 0.5-1.0 mg/kg/week of chronic methotrexate, or 1.5 mg/kg acute dose of dexamethasone.

EXAMPLE 7

Identification of Combinations

As discussed above, compounds of the present invention may be combined with known therapeutic agents, such as analgesics and/or anti-inflammatories, in pharmaceutical compositions. Such analgesics include, but are not limited to, NSAIDS such as salicylates, acetaminophen, ibuprofen and COX-2 inhibitors. Using the Analgesic Bioassay of Example 1, it is expected that one of skill in the art will be able to determine the effectiveness of such combinations as analgesics, and accordingly such combinations are also within the scope of the present invention.

Nomenclature

As will be readily appreciated by one of skill in the art, all stereoisomers of the inventive compounds are included in the present invention. For example, it is believed that there are at least thirty-two possible isomers of compounds of Formulas II and IV.

For example, compounds of Formula II may referred to as 14-(beta-D-glucopyranosyloxy)-4-hydroxy-2,6,10,14-tetramethyl-2,6,10,15-hexadecatetraenoic acid; and may be referred to, with respect to certain isomers, as 14-(beta-D-glucopyranosyloxy)-4-hydroxy-2,6,10,14-tetramethyl-2,6,10,15-hexadecatetraenoic acid [4R/S-(2E,4R/S,6E,10E,14R/S)]. Moreover, the configuration of C-14 has been determined for compounds of Formula II, such that they may be referred to as 14-(beta-D-glucopyranosyloxy)-4-hydroxy-2,6,10,14-tetramethyl-2,6,10,15-hexadecatetraenoic acid [4R/S-(2E,4R/S,6E,10E,14S)].

Likewise, Compounds of Formula IV may be referred to as 14-[(2-O-beta-D-glucopyranosyl-beta-D-glucopyranosyl)oxy]-4-hydroxy-2,6,10,14-tetramethyl-2,6,10,15-hexadecatetraenoic acid; and may be referred to, with respect to certain isomers, as 14-[(2-O-beta-D-glucopyranosyl-beta-D-glucopyranosyl)oxy]-4-hydroxy-2,6,10,14-tetramethyl-2,6,10,15-hexadecatetraenoic acid [4R/S (2E,4R/S,6E,10E,14R/S)]. Moreover, the configuration of C-14 has been determined for compounds of Formula IV, such that they may be referred to as 14-[(2-O-beta-D-glucopyranosyl-beta-D-glucopyranosyl)oxy]-4-hydroxy-2,6,10,14-tetramethyl-2,6,10,15-hexadecatetraenoic acid [4R/S (2E,4R/S,6E,10E,14S)].

The invention has been described herein above with reference to various and specific embodiments and techniques. It will be understood, however, that reasonable modifications of such embodiments and techniques can be made without substantially departing from either the spirit or scope of the invention defined by the following claims. All references cited herein are incorporated in their entirety.

What is claimed is:

1. A method comprising:
   administering to a patient experiencing pain associated with toothache, sprains, strains, burns, injuries, neuropathy, mucosal lesions, or dental procedures a pharmaceutical composition comprising a therapeutically effective inflammation reducing amount of a purified compound according to Formula I:

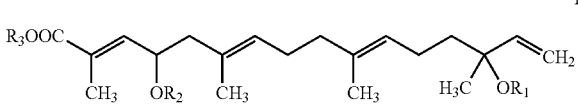

I or a pharmaceutically-acceptable salt, enantiomer, racemic mixture, enantiomerically-enriched mixture, or solvate, of Formula I, in a pharmaceutically effective carrier, wherein
   $R_1$ is selected from the group consisting of glucose, galactose, rhamnose, xylose, and arabinose;

$R_2$ is H; and
$R_3$ is H.

2. A method comprising administering to a patient experiencing pain associated with toothache, sprains, strains, burns, injuries, neuropathy, mucosal lesions, or dental procedures a pharmaceutical composition comprising a therapeutically effective inflammation reducing amount of a purified compound according to Formula III;

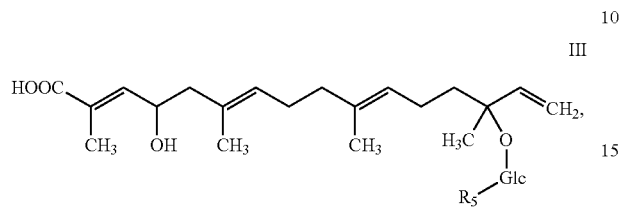

wherein $R_5$ is a hydrolysable sugar.

3. A method according to claim 2, wherein said hydrolysable sugar is glucose.

4. A method according to claim 1, wherein the purified compound according to Formula (I) is present in the composition in an amount of from about 0.01 mg to about 500 mg.

5. A method comprising;
administering to a patient experiencing pain associated with toothache, sprains, strains, burns, injuries, neuropathy, mucosal lesions, or dental procedures a pharmaceutical composition comprising a therapeutically effective inflammation reducing amount of a purified compound according to Formula IV:

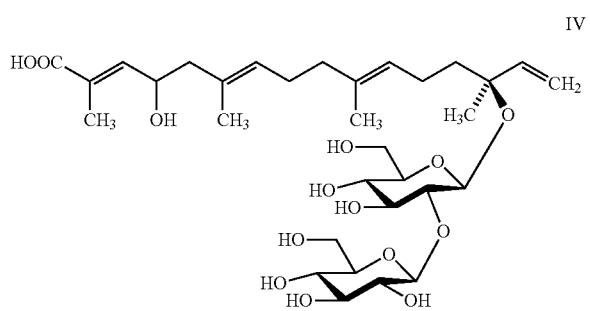

or a pharmaceutically-acceptable salt, enantiomer, racemic mixture, enantiomerically-enriched mixture, or solvate, of Formula IV, in a pharmaceutically effective carrier.

* * * * *